(12) United States Patent
Olivera et al.

(10) Patent No.: US 8,232,535 B2
(45) Date of Patent: Jul. 31, 2012

(54) SYSTEM AND METHOD OF TREATING A PATIENT WITH RADIATION THERAPY

(75) Inventors: Gustavo H. Olivera, Madison, WI (US); Thomas R. Mackie, Verona, WI (US); Jeffrey M. Kapatoes, Madison, WI (US); John H. Hughes, Madison, WI (US); Kenneth J. Ruchala, Madison, WI (US); Paul J. Reckwerdt, Madison, WI (US)

(73) Assignee: Tomotherapy Incorporated, Madison, WI (US)

( * ) Notice: Subject to any disclaimer, the term of this patent is extended or adjusted under 35 U.S.C. 154(b) by 1037 days.

(21) Appl. No.: 11/431,319

(22) Filed: May 10, 2006

(65) Prior Publication Data

US 2006/0285639 A1    Dec. 21, 2006

Related U.S. Application Data

(60) Provisional application No. 60/679,882, filed on May 10, 2005.

(51) Int. Cl.
*G21G 4/00* (2006.01)
(52) U.S. Cl. ........... 250/493.1; 250/491.1; 250/492.1
(58) Field of Classification Search .................. None
See application file for complete search history.

(56) References Cited

U.S. PATENT DOCUMENTS

| | | | |
|---|---|---|---|
| 3,949,265 A | 4/1976 | Holl | |
| 3,964,467 A | 6/1976 | Rose | |
| 4,006,422 A | 2/1977 | Schriber | |
| 4,032,810 A | 6/1977 | Eastham et al. | |
| 4,149,081 A | 4/1979 | Seppi | |
| 4,181,894 A | 1/1980 | Pottier | |
| 4,189,470 A | 2/1980 | Rose | |
| 4,208,185 A | 6/1980 | Sawai et al. | |
| 4,273,867 A | 6/1981 | Lin et al. | |
| 4,314,180 A | 2/1982 | Salisbury | |
| 4,335,465 A | 6/1982 | Christiansen et al. | |
| 4,388,560 A | 6/1983 | Robinson et al. | |
| 4,393,334 A | 7/1983 | Glaser | |
| 4,395,631 A | 7/1983 | Salisbury | |

(Continued)

FOREIGN PATENT DOCUMENTS
CA        2091275        9/1993
(Continued)

OTHER PUBLICATIONS

Ruchala, et al., ("Adaptive IMRT with TomoTherapy", RT Image, Vol.14, No. 25, pp. 14-18, Jun. 18, 2001).*

(Continued)

*Primary Examiner* — Phillip A Johnston
*Assistant Examiner* — Andrew Smyth
(74) *Attorney, Agent, or Firm* — Michael Best & Friedrich LLP

(57) ABSTRACT

A radiation therapy treatment system and method of treating a patient with radiation. The system integrates positioning of the patient, treatment planning, and delivery of the plan. As a result of the integration of imaging capabilities into the treatment apparatus, and efficient processes for contouring and planning, a patient can be treated in approximately 20 minutes or less. The method includes acquiring image data from the patient, defining a target region with one or more predefined shapes, generating a treatment plan based on the defined target region, and delivering radiation to the target region.

100 Claims, 11 Drawing Sheets

U.S. PATENT DOCUMENTS

| | | |
|---|---|---|
| 4,401,765 A | 8/1983 | Craig et al. |
| 4,426,582 A | 1/1984 | Orloff et al. |
| 4,446,403 A | 5/1984 | Cuomo et al. |
| 4,480,042 A | 10/1984 | Craig et al. |
| 4,570,103 A | 2/1986 | Schoen |
| 4,664,869 A | 5/1987 | Mirzadeh et al. |
| 4,703,018 A | 10/1987 | Craig et al. |
| 4,715,056 A | 12/1987 | Vlasbloem et al. |
| 4,736,106 A | 4/1988 | Kashy et al. |
| 4,752,692 A | 6/1988 | Jergenson et al. |
| 4,754,760 A | 7/1988 | Fukukita et al. |
| 4,815,446 A | 3/1989 | McIntosh |
| 4,818,914 A | 4/1989 | Brodie |
| 4,868,844 A | 9/1989 | Nunan |
| 4,870,287 A | 9/1989 | Cole et al. |
| 4,879,518 A | 11/1989 | Broadhurst |
| 4,912,731 A | 3/1990 | Nardi |
| 4,936,308 A | 6/1990 | Fukukita et al. |
| 4,987,309 A | 1/1991 | Klasen et al. |
| 4,998,268 A | 3/1991 | Winter |
| 5,003,998 A | 4/1991 | Collett |
| 5,008,907 A | 4/1991 | Norman et al. |
| 5,012,111 A | 4/1991 | Ueda |
| 5,044,354 A | 9/1991 | Goldhorn et al. |
| 5,065,315 A | 11/1991 | Garcia |
| 5,073,913 A | 12/1991 | Martin |
| 5,084,682 A | 1/1992 | Swenson et al. |
| 5,107,222 A | 4/1992 | Tsuzuki |
| 5,117,829 A | 6/1992 | Miller et al. |
| 5,124,658 A | 6/1992 | Adler |
| 5,138,647 A | 8/1992 | Nguyen et al. |
| 5,210,414 A | 5/1993 | Wallace et al. |
| 5,250,388 A | 10/1993 | Schoch, Jr. et al. |
| 5,317,616 A | 5/1994 | Swerdloff et al. |
| 5,332,908 A | 7/1994 | Weidlich |
| 5,335,255 A | 8/1994 | Seppi et al. |
| 5,346,548 A | 9/1994 | Mehta |
| 5,351,280 A | 9/1994 | Swerdloff et al. |
| 5,382,914 A | 1/1995 | Hamm et al. |
| 5,391,139 A | 2/1995 | Edmundson |
| 5,394,452 A | 2/1995 | Swerdloff et al. |
| 5,405,309 A | 4/1995 | Carden, Jr. |
| 5,442,675 A | 8/1995 | Swerdloff et al. |
| 5,446,548 A | 8/1995 | Gerig et al. |
| 5,453,310 A | 9/1995 | Andersen et al. |
| 5,466,587 A | 11/1995 | Fitzpatrick-McElligott et al. |
| 5,471,516 A | 11/1995 | Nunan |
| 5,483,122 A | 1/1996 | Derbenev et al. |
| 5,489,780 A | 2/1996 | Diamondis |
| 5,511,549 A | 4/1996 | Legg et al. |
| 5,523,578 A | 6/1996 | Herskovic |
| 5,528,650 A | 6/1996 | Swerdloff et al. |
| 5,548,627 A | 8/1996 | Swerdloff et al. |
| 5,552,605 A | 9/1996 | Arata |
| 5,576,602 A | 11/1996 | Hiramoto et al. |
| 5,578,909 A | 11/1996 | Billen |
| 5,579,358 A | 11/1996 | Lin |
| 5,581,156 A | 12/1996 | Roberts et al. |
| 5,596,619 A | 1/1997 | Carol |
| 5,596,653 A | 1/1997 | Kurokawa |
| 5,621,779 A | 4/1997 | Hughes et al. |
| 5,622,187 A | 4/1997 | Carol |
| 5,625,663 A | 4/1997 | Swerdloff et al. |
| 5,627,041 A | 5/1997 | Shartle |
| 5,641,584 A | 6/1997 | Andersen et al. |
| 5,647,663 A | 7/1997 | Holmes |
| 5,651,043 A | 7/1997 | Tsuyuki et al. |
| 5,661,377 A | 8/1997 | Mishin et al. |
| 5,661,773 A | 8/1997 | Swerdloff et al. |
| 5,667,803 A | 9/1997 | Paronen et al. |
| 5,668,371 A | 9/1997 | Deasy et al. |
| 5,673,300 A | 9/1997 | Reckwerdt et al. |
| 5,692,507 A | 12/1997 | Seppi et al. |
| 5,695,443 A | 12/1997 | Brent et al. |
| 5,712,482 A | 1/1998 | Gaiser et al. |
| 5,721,123 A | 2/1998 | Hayes et al. |
| 5,724,400 A | 3/1998 | Swerdloff et al. |
| 5,729,028 A | 3/1998 | Rose |
| 5,734,168 A | 3/1998 | Yao |
| 5,747,254 A | 5/1998 | Pontius |
| 5,751,781 A | 5/1998 | Brown et al. |
| 5,753,308 A | 5/1998 | Andersen et al. |
| 5,754,622 A | 5/1998 | Hughes |
| 5,754,623 A | 5/1998 | Seki |
| 5,760,395 A | 6/1998 | Johnstone |
| 5,800,353 A | 9/1998 | McLaurin, Jr. |
| 5,802,136 A | 9/1998 | Carol |
| 5,811,944 A | 9/1998 | Sampayan et al. |
| 5,815,547 A | 9/1998 | Shepherd et al. |
| 5,818,058 A | 10/1998 | Nakanishi et al. |
| 5,818,902 A | 10/1998 | Yu |
| 5,820,553 A | 10/1998 | Hughes |
| 5,821,051 A | 10/1998 | Androphy et al. |
| 5,821,705 A | 10/1998 | Caporaso et al. |
| 5,823,192 A | 10/1998 | Kalend et al. |
| 5,834,454 A | 11/1998 | Kitano et al. |
| 5,835,562 A | 11/1998 | Ramsdell et al. |
| 5,836,905 A | 11/1998 | Lemelson et al. |
| 5,838,765 A | 11/1998 | Gershman et al. |
| 5,842,175 A | 11/1998 | Andros et al. |
| 5,866,912 A | 2/1999 | Slater et al. |
| 5,870,447 A | 2/1999 | Powell et al. |
| 5,877,023 A | 3/1999 | Sautter et al. |
| 5,877,192 A | 3/1999 | Lindberg et al. |
| 5,901,199 A | 5/1999 | Murphy et al. |
| 5,907,594 A | 5/1999 | Lai |
| 5,912,134 A | 6/1999 | Shartle |
| 5,920,601 A | 7/1999 | Nigg et al. |
| 5,953,461 A | 9/1999 | Yamada |
| 5,962,995 A | 10/1999 | Avnery |
| 5,963,615 A | 10/1999 | Egley et al. |
| 5,969,367 A | 10/1999 | Hiramoto et al. |
| 5,970,499 A * | 10/1999 | Smith et al. ............ 1/1 |
| 5,977,100 A | 11/1999 | Kitano et al. |
| 5,983,424 A | 11/1999 | Naslund |
| 5,986,274 A | 11/1999 | Akiyama et al. |
| 6,011,825 A | 1/2000 | Welch et al. |
| 6,020,135 A | 2/2000 | Levine et al. |
| 6,020,538 A | 2/2000 | Han et al. |
| 6,029,079 A | 2/2000 | Cox et al. |
| 6,038,283 A | 3/2000 | Carol et al. |
| 6,049,587 A | 4/2000 | Leksell et al. |
| 6,066,927 A | 5/2000 | Koudijs |
| 6,069,459 A | 5/2000 | Koudijs |
| 6,071,748 A | 6/2000 | Modlin et al. |
| 6,094,760 A | 8/2000 | Nonaka et al. |
| 6,127,688 A | 10/2000 | Wu |
| 6,152,599 A | 11/2000 | Salter, Jr. |
| 6,171,798 B1 | 1/2001 | Levine et al. |
| 6,178,345 B1 | 1/2001 | Vilsmeier et al. |
| 6,197,328 B1 | 3/2001 | Yanagawa |
| 6,198,957 B1 | 3/2001 | Green |
| 6,200,959 B1 | 3/2001 | Haynes et al. |
| 6,204,510 B1 | 3/2001 | Ohkawa |
| 6,207,400 B1 | 3/2001 | Kwon |
| 6,218,675 B1 | 4/2001 | Akiyama et al. |
| 6,222,905 B1 | 4/2001 | Yoda et al. |
| 6,241,670 B1 | 6/2001 | Nambu |
| 6,242,747 B1 | 6/2001 | Sugitani et al. |
| 6,264,825 B1 | 7/2001 | Blackburn et al. |
| 6,265,837 B1 | 7/2001 | Akiyama et al. |
| 6,279,579 B1 | 8/2001 | Riaziat et al. |
| 6,291,823 B1 | 9/2001 | Doyle et al. |
| 6,301,329 B1 * | 10/2001 | Surridge ............ 378/65 |
| 6,316,776 B1 | 11/2001 | Hiramoto et al. |
| 6,319,469 B1 | 11/2001 | Mian et al. |
| 6,322,249 B1 | 11/2001 | Wofford et al. |
| 6,324,243 B1 | 11/2001 | Edic et al. |
| 6,331,194 B1 | 12/2001 | Sampayan et al. |
| 6,345,114 B1 | 2/2002 | Mackie et al. |
| 6,360,116 B1 | 3/2002 | Jackson, Jr. et al. |
| 6,385,286 B1 | 5/2002 | Fitchard et al. |
| 6,385,288 B1 | 5/2002 | Kanematsu |
| 6,393,096 B1 | 5/2002 | Carol et al. |
| 6,405,072 B1 | 6/2002 | Cosman |
| 6,407,505 B1 | 6/2002 | Bertsche |
| 6,417,178 B1 | 7/2002 | Klunk et al. |

| | | |
|---|---|---|
| 6,424,856 B1 | 7/2002 | Vilsmeier et al. |
| 6,428,547 B1 | 8/2002 | Vilsmeier et al. |
| 6,433,349 B2 | 8/2002 | Akiyama et al. |
| 6,438,202 B1 | 8/2002 | Olivera et al. |
| 6,455,844 B1 | 9/2002 | Meyer |
| 6,462,490 B1 | 10/2002 | Matsuda et al. |
| 6,465,957 B1 | 10/2002 | Whitham et al. |
| 6,466,644 B1 | 10/2002 | Hughes et al. |
| 6,469,058 B1 | 10/2002 | Grove et al. |
| 6,472,834 B2 | 10/2002 | Hiramoto et al. |
| 6,473,490 B1 | 10/2002 | Siochi |
| 6,475,994 B2 | 11/2002 | Tomalia et al. |
| 6,477,229 B1 | 11/2002 | Grosser |
| 6,482,604 B2 | 11/2002 | Kwon |
| 6,484,144 B2 | 11/2002 | Martin et al. |
| 6,487,274 B2 | 11/2002 | Bertsche |
| 6,493,424 B2 | 12/2002 | Whitham |
| 6,497,358 B1 | 12/2002 | Walsh |
| 6,498,011 B2 | 12/2002 | Hohn et al. |
| 6,500,343 B2 | 12/2002 | Siddiqi |
| 6,504,899 B2 | 1/2003 | Pugachev et al. |
| 6,510,199 B1 | 1/2003 | Hughes et al. |
| 6,512,942 B1 | 1/2003 | Burdette et al. |
| 6,516,046 B1 | 2/2003 | Frohlich et al. |
| 6,527,443 B1 | 3/2003 | Vilsmeier et al. |
| 6,531,449 B2 | 3/2003 | Khojasteh et al. |
| 6,535,837 B1 | 3/2003 | Schach Von Wittenau |
| 6,552,338 B1 | 4/2003 | Doyle |
| 6,558,961 B1 | 5/2003 | Sarphie et al. |
| 6,560,311 B1 | 5/2003 | Shepard et al. |
| 6,562,376 B2 | 5/2003 | Hooper et al. |
| 6,568,449 B2 | 5/2003 | Owen et al. |
| 6,584,174 B2 | 6/2003 | Schubert et al. |
| 6,586,409 B1 | 7/2003 | Wheeler |
| 6,605,297 B2 | 8/2003 | Nadachi et al. |
| 6,611,700 B1 | 8/2003 | Vilsmeier et al. |
| 6,617,768 B1 | 9/2003 | Hansen |
| 6,618,467 B1 | 9/2003 | Ruchala et al. |
| 6,621,889 B1 | 9/2003 | Mostafavi |
| 6,633,686 B1 | 10/2003 | Bakircioglu et al. |
| 6,634,790 B1 | 10/2003 | Salter, Jr. |
| 6,636,622 B2 | 10/2003 | Mackie et al. |
| 6,637,056 B1 | 10/2003 | Tybinkowski et al. |
| 6,646,383 B2 | 11/2003 | Bertsche et al. |
| 6,653,547 B2 | 11/2003 | Akamatsu |
| 6,661,870 B2 | 12/2003 | Kapatoes et al. |
| 6,688,187 B1 | 2/2004 | Masquelier |
| 6,690,965 B1 | 2/2004 | Riaziat et al. |
| 6,697,452 B2 | 2/2004 | Xing |
| 6,705,984 B1 | 3/2004 | Angha |
| 6,708,184 B2 * | 3/2004 | Smith et al. ............................ 1/1 |
| 6,713,668 B2 | 3/2004 | Akamatsu |
| 6,713,976 B1 | 3/2004 | Zumoto et al. |
| 6,714,620 B2 | 3/2004 | Caflisch et al. |
| 6,714,629 B2 | 3/2004 | Vilsmeier |
| 6,716,162 B2 | 4/2004 | Hakamata |
| 6,719,683 B2 | 4/2004 | Frohlich |
| 6,723,334 B1 | 4/2004 | McGee et al. |
| 6,731,970 B2 | 5/2004 | Schlossbauer et al. |
| 6,741,674 B2 | 5/2004 | Lee |
| 6,760,402 B2 | 7/2004 | Ghelmansarai |
| 6,774,383 B2 | 8/2004 | Norimine et al. |
| 6,787,771 B2 | 9/2004 | Bashkirov et al. |
| 6,787,983 B2 | 9/2004 | Yamanobe et al. |
| 6,788,764 B2 | 9/2004 | Saladin et al. |
| 6,792,073 B2 | 9/2004 | Deasy et al. |
| 6,792,074 B2 | 9/2004 | Erbel et al. |
| 6,796,164 B2 | 9/2004 | McLoughlin et al. |
| 6,800,866 B2 | 10/2004 | Amemiya et al. |
| 6,804,548 B2 | 10/2004 | Takahashi et al. |
| 6,822,244 B2 | 11/2004 | Beloussov et al. |
| 6,822,247 B2 | 11/2004 | Sasaki |
| 6,838,676 B1 | 1/2005 | Jackson |
| 6,842,502 B2 | 1/2005 | Jaffray et al. |
| 6,844,689 B1 | 1/2005 | Brown et al. |
| 6,865,253 B2 | 3/2005 | Blumhofer et al. |
| 6,865,254 B2 | 3/2005 | Nafstadius |
| 6,865,411 B2 | 3/2005 | Erbel et al. |
| 6,869,428 B2 * | 3/2005 | Sagehashi et al. ................. 606/4 |
| 6,871,171 B1 | 3/2005 | Agur et al. |
| 6,873,115 B2 | 3/2005 | Sagawa et al. |
| 6,873,123 B2 | 3/2005 | Marchand et al. |
| 6,878,951 B2 | 4/2005 | Ma |
| 6,882,702 B2 | 4/2005 | Luo |
| 6,882,705 B2 | 4/2005 | Egley et al. |
| 6,888,326 B2 | 5/2005 | Amaldi et al. |
| 6,889,695 B2 * | 5/2005 | Pankratov et al. ............ 128/898 |
| 6,891,178 B2 | 5/2005 | Xing |
| 6,898,456 B2 | 5/2005 | Erbel |
| 6,904,125 B2 | 6/2005 | Van Dyk et al. |
| 6,907,282 B2 | 6/2005 | Siochi |
| 6,922,455 B2 | 7/2005 | Jurczyk et al. |
| 6,929,398 B1 * | 8/2005 | Tybinkowski et al. ......... 378/209 |
| 6,932,807 B1 * | 8/2005 | Tomita et al. .................... 606/10 |
| 6,936,832 B2 | 8/2005 | Norimine et al. |
| 6,955,464 B1 | 10/2005 | Tybinkowski et al. |
| 6,963,171 B2 | 11/2005 | Sagawa et al. |
| 6,963,771 B2 | 11/2005 | Scarantino et al. |
| 6,974,254 B2 | 12/2005 | Paliwal et al. |
| 6,977,984 B2 | 12/2005 | Hsieh et al. |
| 6,984,835 B2 | 1/2006 | Harada |
| 6,990,167 B2 | 1/2006 | Chen |
| 7,015,490 B2 | 3/2006 | Wang et al. |
| 7,046,762 B2 | 5/2006 | Lee |
| 7,046,831 B2 | 5/2006 | Ruchala et al. |
| 7,051,605 B2 | 5/2006 | Lagraff et al. |
| 7,060,997 B2 | 6/2006 | Norimine et al. |
| 7,077,569 B1 | 7/2006 | Tybinkowski et al. |
| 7,081,619 B2 | 7/2006 | Bashkirov et al. |
| 7,084,410 B2 | 8/2006 | Beloussov et al. |
| 7,087,200 B2 | 8/2006 | Taboas et al. |
| 7,092,482 B2 | 8/2006 | Besson |
| 7,112,924 B2 | 9/2006 | Hanna |
| 7,130,372 B2 | 10/2006 | Kusch et al. |
| 7,154,991 B2 | 12/2006 | Earnst et al. |
| 7,158,692 B2 | 1/2007 | Chalana et al. |
| 7,186,986 B2 | 3/2007 | Hinderer et al. |
| 7,186,991 B2 | 3/2007 | Kato et al. |
| 7,203,272 B2 | 4/2007 | Chen |
| 7,209,547 B2 | 4/2007 | Baier et al. |
| 7,221,729 B2 | 5/2007 | Wakai et al. |
| 7,221,733 B1 * | 5/2007 | Takai et al. ....................... 378/65 |
| 7,252,307 B2 | 8/2007 | Kanbe et al. |
| 7,257,196 B2 | 8/2007 | Brown et al. |
| 7,265,356 B2 * | 9/2007 | Pelizzari et al. ......... 250/370.09 |
| 7,280,630 B2 | 10/2007 | Chen |
| 7,302,033 B2 * | 11/2007 | Carrano et al. ................. 378/41 |
| 7,333,588 B2 | 2/2008 | Mistretta et al. |
| 7,367,955 B2 | 5/2008 | Zhang et al. |
| 7,391,026 B2 | 6/2008 | Trinkaus et al. |
| 7,391,849 B2 * | 6/2008 | Smith ........................... 378/109 |
| 7,412,029 B2 | 8/2008 | Myles |
| 7,413,873 B2 | 8/2008 | Waterman et al. |
| 7,444,011 B2 * | 10/2008 | Pan et al. ...................... 382/131 |
| 7,492,858 B2 | 2/2009 | Partain et al. |
| 7,983,380 B2 | 7/2011 | Guertin et al. |
| 2002/0193685 A1 | 12/2002 | Mate et al. |
| 2003/0048868 A1 * | 3/2003 | Bailey et al. ..................... 378/65 |
| 2003/0086527 A1 | 5/2003 | Speiser et al. |
| 2003/0105650 A1 | 6/2003 | Lombardo et al. |
| 2003/0112922 A1 | 6/2003 | Burdette et al. |
| 2004/0010418 A1 | 1/2004 | Buonocore et al. |
| 2004/0024300 A1 | 2/2004 | Graf |
| 2004/0057119 A1 * | 3/2004 | Sagehashi et al. ............ 359/618 |
| 2004/0068182 A1 | 4/2004 | Misra |
| 2004/0096033 A1 | 5/2004 | Seppi et al. |
| 2004/0116804 A1 | 6/2004 | Mostafavi |
| 2004/0120452 A1 * | 6/2004 | Shapiro et al. ................... 378/19 |
| 2004/0131150 A1 * | 7/2004 | Pankratov et al. .............. 378/65 |
| 2004/0165696 A1 * | 8/2004 | Lee .................................. 378/65 |
| 2004/0254448 A1 | 12/2004 | Amies et al. |
| 2004/0254773 A1 | 12/2004 | Zhang et al. |
| 2005/0031181 A1 | 2/2005 | Bi et al. |
| 2005/0080332 A1 | 4/2005 | Shiu et al. |
| 2005/0096515 A1 | 5/2005 | Geng |
| 2005/0143965 A1 * | 6/2005 | Failla et al. ........................ 703/2 |
| 2005/0161051 A1 * | 7/2005 | Pankratov et al. ............ 128/898 |
| 2005/0171396 A1 * | 8/2005 | Pankratov et al. ................ 600/1 |

| | | | |
|---|---|---|---|
| 2005/0180544 A1* | 8/2005 | Sauer et al. | 378/195 |
| 2005/0197564 A1* | 9/2005 | Dempsey | 600/411 |
| 2005/0251029 A1 | 11/2005 | Khamene et al. | |
| 2006/0074292 A1 | 4/2006 | Thomson et al. | |
| 2006/0078086 A1 | 4/2006 | Riley et al. | |
| 2006/0083349 A1 | 4/2006 | Harari et al. | |
| 2006/0100738 A1 | 5/2006 | Alsafadi et al. | |
| 2006/0133568 A1 | 6/2006 | Moore | |
| 2006/0153330 A1* | 7/2006 | Wong et al. | 378/65 |
| 2006/0193441 A1 | 8/2006 | Cadman | |
| 2006/0215813 A1 | 9/2006 | Scherch et al. | |
| 2006/0241332 A1 | 10/2006 | Klein et al. | |
| 2006/0285639 A1* | 12/2006 | Olivera et al. | 378/65 |
| 2006/0293583 A1 | 12/2006 | Saracen et al. | |
| 2007/0003007 A1* | 1/2007 | Carrano et al. | 378/41 |
| 2007/0036418 A1* | 2/2007 | Pan et al. | 382/131 |
| 2007/0041494 A1 | 2/2007 | Ruchala et al. | |
| 2007/0041495 A1 | 2/2007 | Olivera et al. | |
| 2007/0041496 A1 | 2/2007 | Olivera et al. | |
| 2007/0041497 A1 | 2/2007 | Schnarr et al. | |
| 2007/0041498 A1 | 2/2007 | Olivera et al. | |
| 2007/0041499 A1 | 2/2007 | Lu et al. | |
| 2007/0041500 A1 | 2/2007 | Olivera et al. | |
| 2007/0043286 A1 | 2/2007 | Lu et al. | |
| 2007/0076846 A1 | 4/2007 | Ruchala et al. | |
| 2007/0078306 A1* | 4/2007 | Allison et al. | 600/300 |
| 2007/0088573 A1 | 4/2007 | Ruchala et al. | |
| 2007/0104316 A1 | 5/2007 | Ruchala et al. | |
| 2007/0127623 A1 | 6/2007 | Goldman et al. | |
| 2007/0127790 A1 | 6/2007 | Lau et al. | |
| 2007/0156453 A1 | 7/2007 | Frielinghaus et al. | |
| 2007/0189591 A1 | 8/2007 | Lu et al. | |
| 2007/0195922 A1 | 8/2007 | Mackie et al. | |
| 2007/0195929 A1 | 8/2007 | Ruchala et al. | |
| 2007/0195930 A1 | 8/2007 | Kapatoes et al. | |
| 2007/0197908 A1 | 8/2007 | Ruchala et al. | |
| 2007/0201613 A1 | 8/2007 | Lu et al. | |
| 2007/0211857 A1 | 9/2007 | Urano et al. | |
| 2007/0238957 A1 | 10/2007 | Yared | |
| 2007/0248214 A1* | 10/2007 | Smith | 378/109 |
| 2008/0002811 A1* | 1/2008 | Allison | 378/65 |
| 2008/0279328 A1 | 11/2008 | Zeitler et al. | |

FOREIGN PATENT DOCUMENTS

| | | |
|---|---|---|
| CA | 2180227 | 12/1996 |
| WO | 03/076003 | 9/2003 |
| WO | 2004/057515 | 7/2004 |

OTHER PUBLICATIONS

Anthony Yezzi, et al., "A Variational Framework for Joint Segmentation and Registration", Mathematical Method in Biomedical Image Analysis, 8 pages, 2001.

Ronald D. Rogus, et al., "Accuracy of a Photogrammetry-Based Patient Positioning and Monitoring System for Radiation Therapy", Medical Physics, vol. 26, Issue 5, 2 pages, May 1999.

D. Rueckert, et al., "Nonrigid Registration Using Free-Form Deformations: Applications to Breast MR Images", IEEE Transactions on Medical Imaging, vol. 18, No. 8, pp. 712-721, Aug. 1999.

Yuan-Nan Young, "Registration-Based Morphing of Active Contours for Segmentation of CT Scans", Mathematical Biosciences and Engineering, vol. 2, No. 1, pp. 79-96, Jan. 2005.

Marcelo Bertalmio, et al., "Morphing Active Contours", IEEE Transactions on Pattern Analysis and Machine Intelligence, vol. 22, No. 7, pp. 733-737, Jul. 2000.

Kenneth Ruchala, et al., "Adaptive IMRT with TomoTherapy", RT Image, vol. 14, No. 25, pp. 14-18, Jun. 18, 2001.

Lu, W., et al., "Automatic Re-Contouring in 4D Radiotherapy", Physical Medical Biology, Mar. 7, 2006, 51 (5):1077-99.

Lu, W., et al., 2004 Automatic Re-Contouring for 4-D Planning and Adaptive Radiotherapy, The 90th RSNA Meeting, Chicago, Illinois, (abstract: Radiology 227 (p) 543).

Lu, W., et al., 2004 Automatic Re-Contouring Regions of Interest Based on Deformable Registration and Surface Reconstruction, AAPM 2004, (abstract: Medical Physics 31, 1845-6).

Purdy, James, "3D Treatment Planning and Intensity-Modulated Radiation Therapy," Oncology, vol. 13, No. 10, suppl. 5 (Oct. 1999).

Lee, Jason et al., "Intensity Modulated Radiation Therapy; An Introduction for Patients and Clinicians," www.oncolink.com/templates/treatment/article.cfm?c=45&s=33&id=182; Jun. 16, 2001.

Keall, Paul, "4-Dimensional Computed Tomography Imaging and Treatment Planning," Seminars in Radiation Oncology, vol. 14, No. 1, Jan. 2004; pp. 81-90.

Mackie, T. Rockwell et al., "Tomotherapy" Seminars in Radiation Oncology, vol. 9, No. 1, Jan. 1, 1999, pp. 108-117, XP002603992.

Miller, Karen, "The Phantom Torso", RT Image, vol. 14 No. 25, Jun. 18, 2001.

Wells III, William et al., "Multi-Modal Volume Registration by Maximization of Mutual Information," Medical Image Analysis, Oxford University Press (1996).

Michalski, Jeff M. et al., Three-Dimensional Conformal Radiation Therapy (3DCRT) for Prostate Cancer,: The Prostate Cancer InfoLink, Jul. 6, 1996.

* cited by examiner

Fig. 8

SYSTEM AND METHOD OF TREATING A PATIENT WITH RADIATION THERAPY

RELATED APPLICATIONS

This application is a non-provisional application claiming priority to prior filed Provisional Patent Application Ser. No. 60/679,882, filed on May 10, 2005, the entire contents of which are incorporated herein by reference. The entire contents of U.S. Pat. Nos. 5,317,616; 5,351,280; 5,394,452; 5,442,675; 5,548,627; 5,528,650; 5,625,663; 5,647,663; 5,661,773; 5,673,300; 5,724,400; 6,385,286; 6,438,202; 6,618,467; 6,636,622 are incorporated herein by reference.

BACKGROUND OF THE INVENTION

Over the past decades, improvements in computers and networking, radiation therapy treatment planning software, and medical imaging modalities (CT, MRI, US, and PET) have been incorporated into radiation therapy practice. These improvements have led to the development of image guided radiation therapy ("IGRT"). IGRT is radiation therapy that uses images of the patient's internal anatomy to better target the radiation dose in the tumor while reducing the radiation exposure to healthy organs. The radiation dose delivered to the tumor is controlled with intensity modulated radiation therapy ("IMRT"), which involves changing the size, shape, and intensity of the radiation beam to conform to the size, shape, and location of the patient's tumor. IGRT and IMRT lead to improved control of the tumor while simultaneously reducing the potential for acute side effects due to irradiation of healthy tissue surrounding the tumor.

IMRT is becoming the standard of care in several countries. However, in many situations, IMRT is not used to treat a patient due to time, resource, and billing constraints. Daily images of the patient can be used to guarantee that the high gradients generated by IMRT plans are located on the correct position for patient treatment. Also these images can provide necessary information to adapt the plan online or offline if needed.

SUMMARY OF THE INVENTION

In a medical facility, there are certain palliative and emergency cases that need to be simulated and treated on the same day. The average time for treatment for these patients is approximately one hour for conventional external beam radiation therapy and typically requires separate pieces of equipment for imaging, planning, and treating the patient. In general, IMRT and IGRT are not used with these patients because these processes can be time and resource consuming, and speed is a high priority for these cases.

Simple conformal or IMRT plans can be generated with images obtained at the time of first treatment with minimal computation times for optimized treatment delivery. Patients can benefit from the advantages of conformal therapy, IMRT and IGRT, such as lower side effects and still have a decreased time and lower cost to image, plan, and deliver radiation therapy.

One embodiment of the invention includes a method of treating a patient with radiation. The method comprises the acts of acquiring image data from the patient, defining a target region, generating a treatment plan based on the defined target region, and delivering radiation to the target region. The acts of acquiring image data from the patient and delivering radiation to the target region are performed by essentially the same apparatus.

Another embodiment of the invention includes a method of treating a patient with radiation. The method comprises the acts of acquiring first image data for a patient on a first apparatus, generating a contour and a treatment plan for the patient based upon the first image data, positioning the patient on a second apparatus, acquiring second image data for the patient on the second apparatus, calculating the dose to be delivered to the patient based on the second image data, delivering radiation to the patient using the second apparatus.

Another embodiment of the invention includes a computer program stored on a computer readable medium capable of being executed by a computer. The computer program is for use in a radiation therapy treatment system. The computer program comprises an image module, a contour module, a treatment plan module, and a delivery module. The image acquisition module is operable to acquire images of a patient. The contour module is operable to define a target region. The treatment plan module is operable to analyze and generate a treatment plan based on the target region as defined by the selected shapes. The delivery module is operable to deliver radiation to the patient based on the treatment plan.

Another embodiment of the invention includes a method of treating a patient with radiation. The method comprises the acts of acquiring image data from the patient, defining a target region with one or more predefined shapes, applying a pre-optimized dose distribution to the defined target region, shifting the dose distribution based on the selected one or more predefined shapes, generating a treatment plan based on the defined target region and the dose distribution, and delivering radiation to the target region, wherein the imaging and treatment is performed on essentially the same apparatus.

Other independent aspects of the invention will become apparent by consideration of the detailed description and accompanying drawings.

BRIEF DESCRIPTION OF THE DRAWINGS

FIG. 8 is a screen shot generated by the software program of FIG. 4.

DETAILED DESCRIPTION

Figure 1:
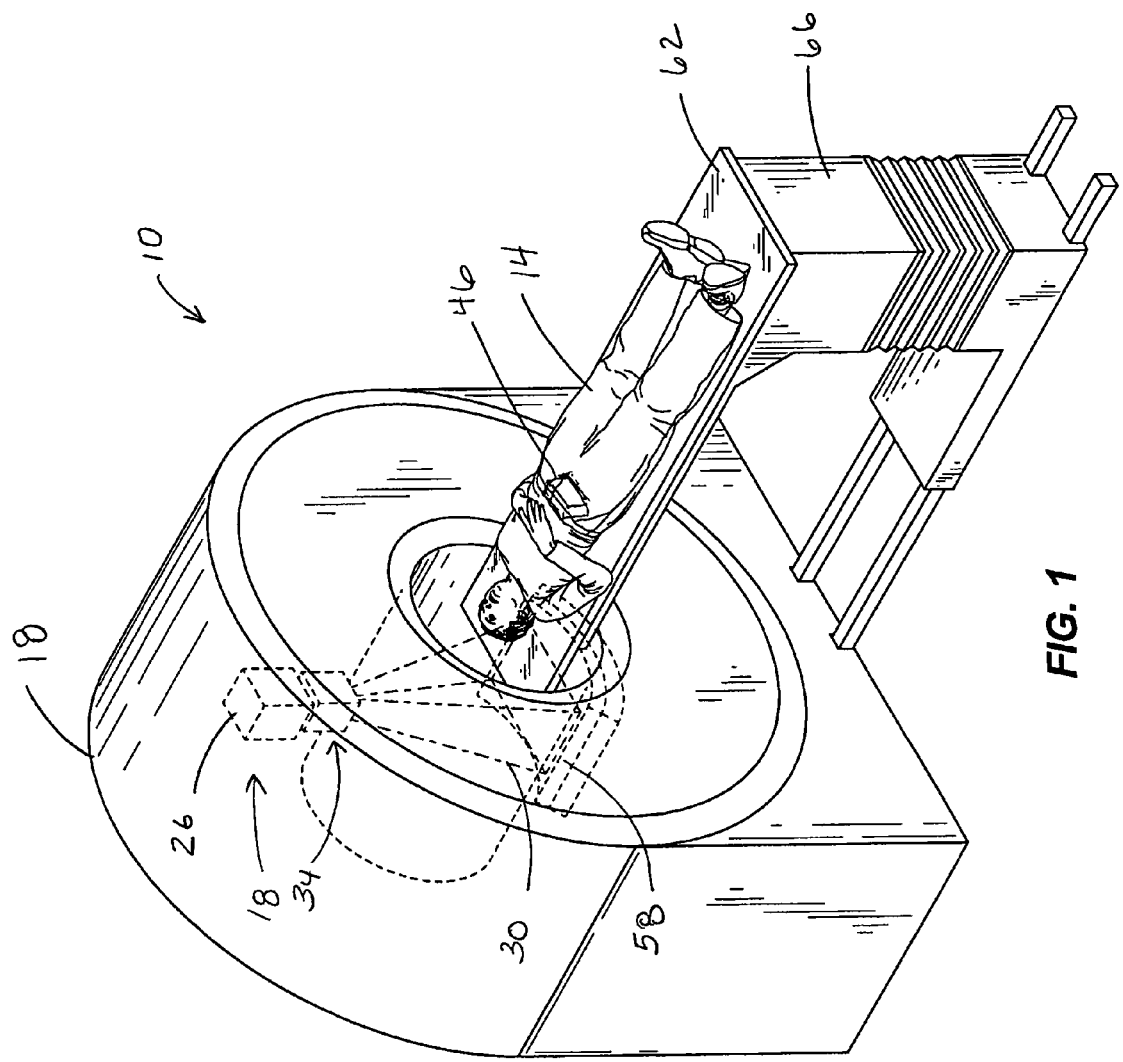
FIG. 1 is a perspective view of a radiation therapy treatment system according to one embodiment of the invention.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising" or "having" and variations thereof herein is meant to encompass the items listed thereafter and equivalents thereof as well as additional items. The terms "mounted," "connected" and "coupled" are used broadly and encompass both direct and indirect mounting, connecting and coupling. Further, "connected" and "coupled" are not restricted to physical or mechanical connections or couplings, and can include electrical connections or couplings, whether direct or indirect.

In addition, it should be understood that embodiments of the invention include both hardware, software, and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic based aspects of the invention may be implemented in software. As such, it should be noted that a plurality of hardware and software based devices, as well as a plurality of different structural components may be utilized to implement the invention. Furthermore, and as described in subsequent paragraphs, the specific mechanical configurations illustrated in the drawings are intended to exemplify embodiments of the invention and that other alternative mechanical configurations are possible.

FIG. 1 illustrates a radiation therapy treatment system 10 that can provide radiation therapy to a patient 14. The radiation therapy treatment system 10 includes a gantry 18. The gantry 18 can support a radiation source 22. The radiation source 22 can include a linear accelerator 26 operable to generate a beam 30 of photon radiation. The radiation source 22 can also include a modulation device 34 operable to modify or modulate the radiation beam 30. The modulation device 34 provides the modulation needed for IMRT.

Figure 2:
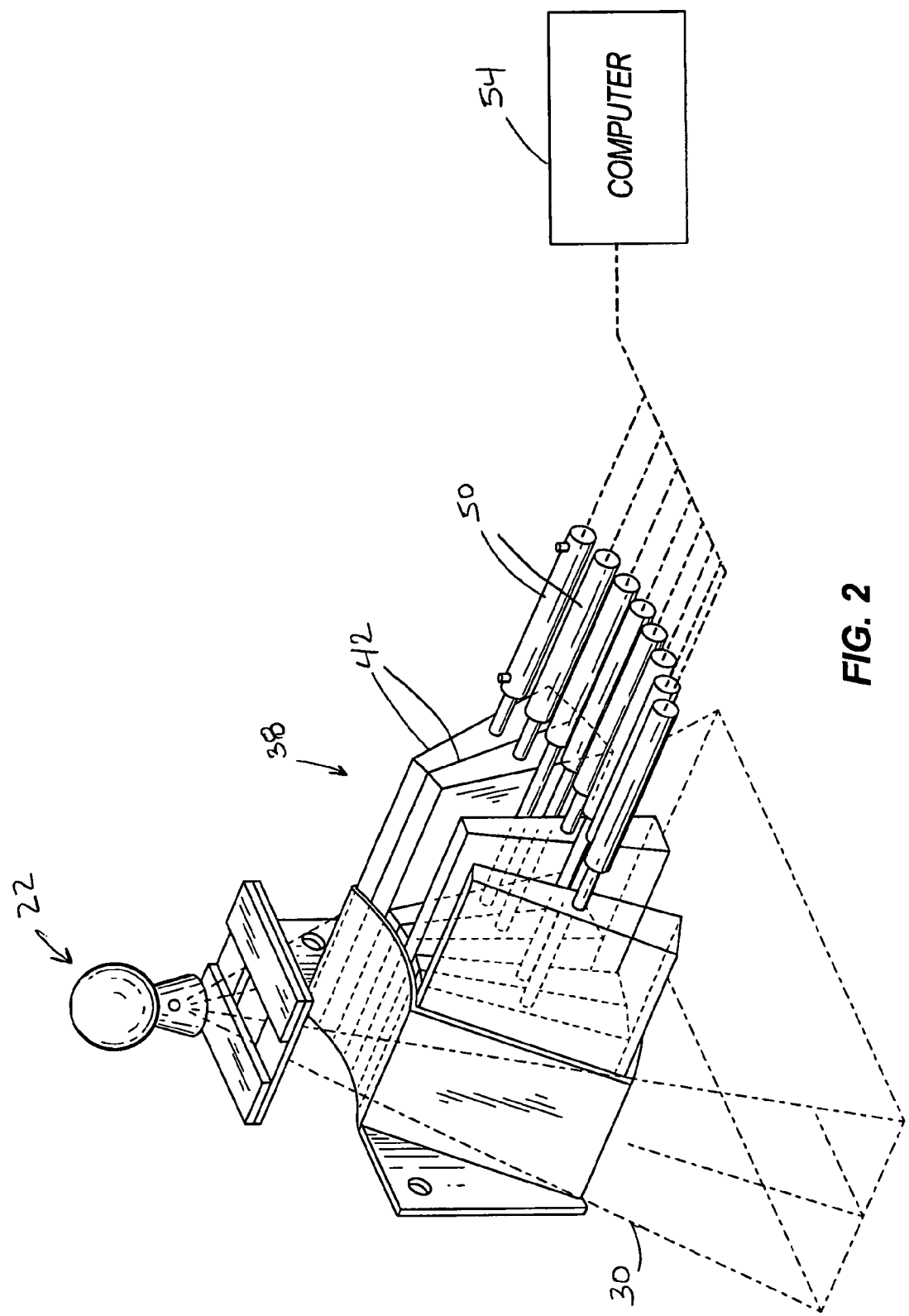
FIG. 2 is a perspective view of a multi-leaf collimator that can be used in the radiation therapy treatment system illustrated in FIG. 1.

In one embodiment, and illustrated in FIG. 2, the modulation device 34 can comprise a multi-leaf collimator 38, which includes a plurality of interlaced leaves 42 operable to move from position to position, to provide intensity modulation. It is also noted that the leaves 42 can be moved to a position anywhere between a minimally and maximally-open position. The plurality of interlaced leaves 42 modulate the strength, size, and shape of the radiation beam 30 before the radiation beam 30 reaches a target 46 on the patient 14. Each of the leaves 42 is independently controlled by an actuator 50, such as a motor or an air valve so that the leaf 42 can open and close quickly to permit or block the passage of radiation. The actuators 50 can be controlled by a computer 54 and/or controller.

The radiation therapy treatment system 10 can also include a detector 58, e.g., a kilovoltage or a megavoltage detector, operable to receive the radiation beam 30. The linear accelerator 26 and the detector 58 can also operate as a computed tomography (CT) system to generate CT images of the patient 14. The linear accelerator 26 emits the radiation beam 30 toward the target 46 in the patient 14. The target 46 and surrounding tissues absorb some of the radiation. The detector 58 detects or measures the amount of radiation absorbed by the target 46 and the surrounding tissues. The detector 58 collects the absorption data from different angles as the linear accelerator 26 rotates around and emits radiation toward the patient 14. The collected absorption data is transmitted to the computer 54 to process the absorption data and to generate cross-sectional images or "slices" of the patient's body tissues and organs. The images can also illustrate bone, soft tissues and blood vessels.

The CT images can be acquired with a radiation beam 30 that has a fan-shaped geometry, a multi-slice geometry or a cone-beam geometry. In addition, the CT images can be acquired with the linear accelerator 26 delivering megavoltage energies or kilovoltage energies. It is also noted that the acquired CT images can be registered with previously acquired CT images (from the radiation therapy treatment system 10 or other image acquisition devices, such as other CT scanners, MRI systems, and PET systems). For example, the previously acquired CT images for the patient 14 can include identified regions of interest and/or regions at risk made through a contouring process (described below). The newly acquired CT images for the patient 14 can be registered with the previously acquired CT images to assist in identifying the regions of interest and/or regions at risk in the new CT images. The registration process can use rigid or deformable registration tools.

In some embodiments, the radiation therapy treatment system 10 can include an x-ray source and a CT image detector. The x-ray source and the CT image detector operate in a similar manner as the linear accelerator 26 and the detector 58 as described above to acquire image data. The image data is transmitted to the computer 54 where it is processed to generate cross-sectional images or "slices" of the patient's body tissues and organs.

The radiation therapy treatment system 10 can also include a couch 62 (illustrated in FIG. 1), which supports the patient 14 and a drive system 66 operable to manipulate the location of the couch 62. The drive system 66 can be controlled by the computer 54.

Figure 3:
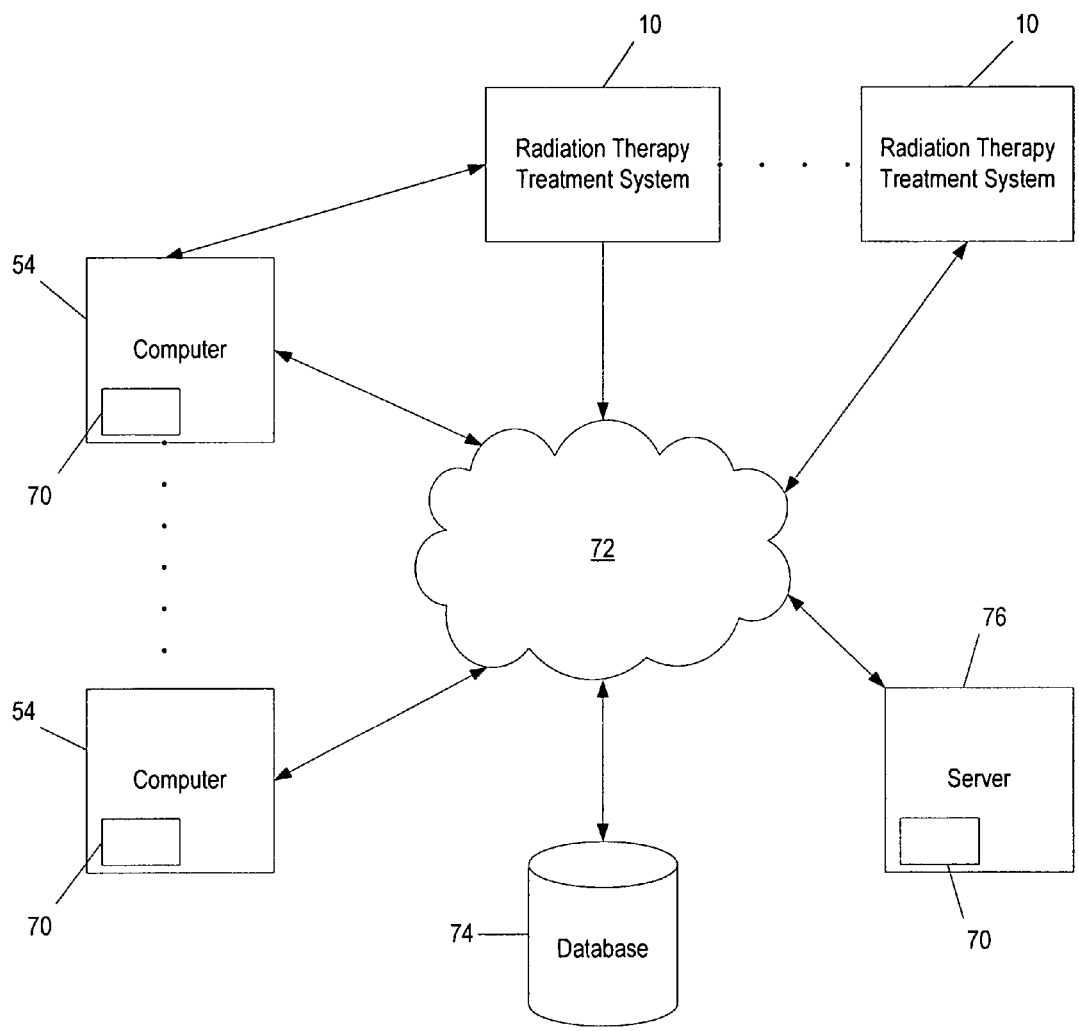
FIG. 3 is a schematic illustration of the radiation therapy treatment system in a networked configuration.

The computer 54, illustrated in FIG. 3, includes an operating system for running various software programs and/or a communications application. In particular, the computer 54 can include a software program(s) 70 that operates to communicate with the radiation therapy treatment system 10. The computer 54 can include any suitable input/output device adapted to be accessed by medical personnel. The computer 54 can include typical hardware such as a processor, I/O interfaces, and storage devices or memory. The computer 54 can also include input devices such as a keyboard and a mouse. The computer 54 can further include standard output devices, such as a monitor. In addition, the computer 54 can include peripherals, such as a printer and a scanner.

The computer 54 can be networked with other computers 54 and radiation therapy treatment systems 10. The computers 54 and radiation therapy treatment system 10 can communicate with a network 72. The computers 54 and radiation therapy treatment systems 10 can also communicate with a database(s) 74 and a server(s) 76. It is noted that the software program(s) 70 could also reside on the server(s) 76.

The network 72 can be built according to any networking technology or topology or combinations of technologies and topologies and can include multiple sub-networks. Connections between the computers and systems shown in FIG. 3 can be made through local area networks ("LANs"), wide area networks ("WANs"), public switched telephone networks ("PSTNs"), Intranets, the Internet, or any other suitable networks. In a hospital or medical care facility, communication between the computers and systems shown in FIG. 3 can be made through the Health Level Seven ("HL7") protocol with any version and/or other required protocol. HL7 is a standard protocol which specifies the implementation of interfaces between two computer applications (sender and receiver) from different vendors for electronic data exchange in health care environments. HL7 can allow health care institutions to exchange key sets of data from different application systems. Specifically, HL7 can define the data to be exchanged, the timing of the interchange, and the communication of errors to the application. The formats are generally generic in nature and can be configured to meet the needs of the applications involved.

Communication between the computers and systems shown in FIG. 3 can also occur through the Digital Imaging and Communications in Medicine (DICOM) protocol with any version and/or other required protocol. DICOM is an international communications standard developed by NEMA that defines the format used to transfer medical image-related data between different pieces of medical equipment. DICOM RT refers to the standards that are specific to radiation therapy data.

The two-way arrows in FIG. 3 generally represent two-way communication and information transfer between the network 72 and any one of the computers 54 and the systems 10 shown in FIG. 3. However, for some medical equipment, only one-way communication and information transfer may be necessary.

Figure 4:
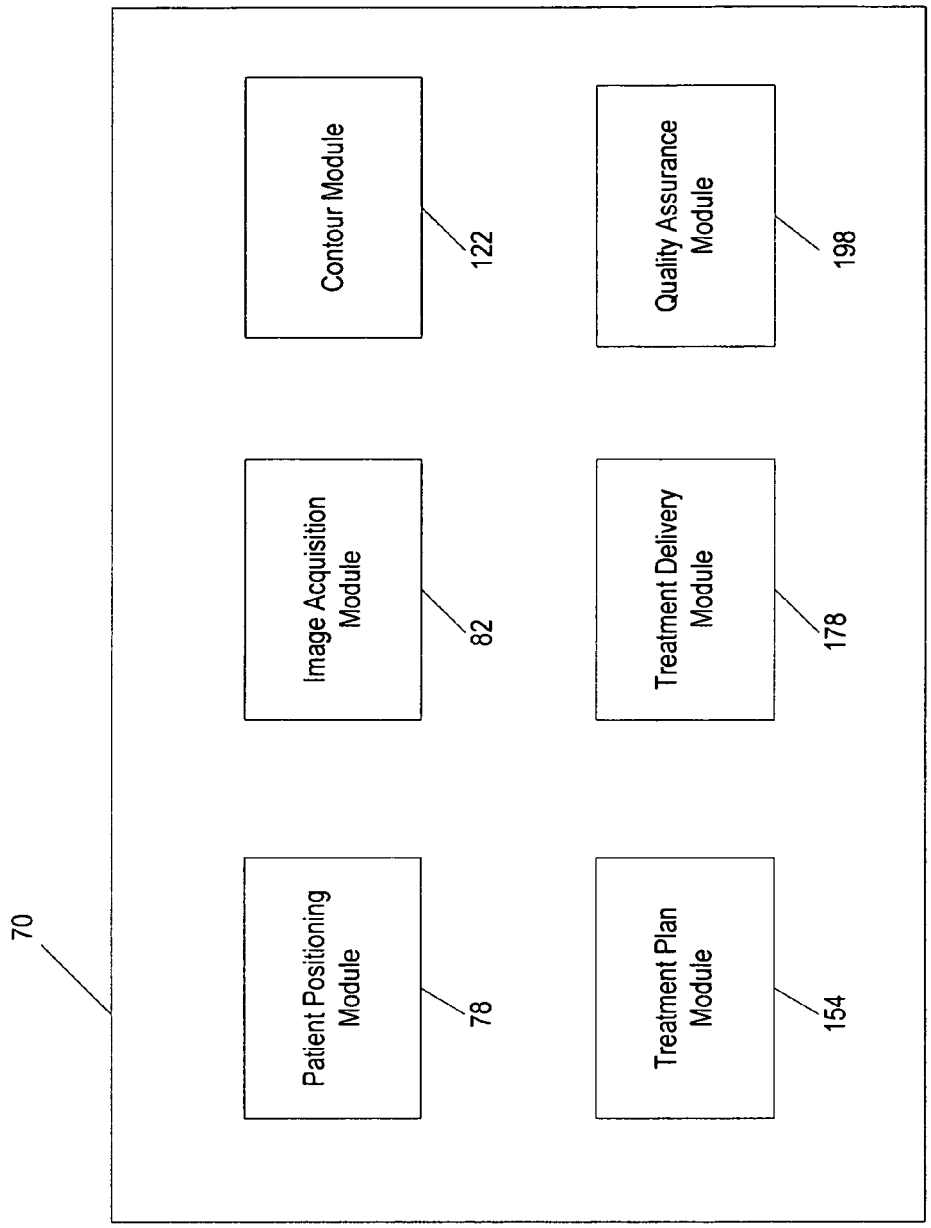
FIG. 4 is a block diagram of a software program that can be used in the radiation therapy treatment system of FIG. 1.

The software program 70, schematically illustrated in FIG. 4, includes a patient positioning module 78 operable to provide instructions to the drive system 66 to move the couch 62. The patient positioning module 78 can receive data from lasers positioned in the treatment room to provide patient position data with respect to the isocenter of the gantry 18. Based on the data from the lasers, the patient positioning module 78 provides instructions to the drive system 66, which moves the couch 62 to achieve proper alignment of the patient 14 with respect to the gantry 18. It is noted that devices and systems, other than lasers, can be used to provide data to the patient positioning module 78 to assist in the alignment process.

The software program 70 also includes an image acquisition module 82 operable to acquire and process the absorption data generated when the linear accelerator 26 delivers the radiation beam 30 toward the target 46 and the detector 58 detects the amount of radiation absorbed by the target 46 and the surrounding tissues. The image acquisition module 82 processes the absorption data to generate the CT images and displays the images on the computer monitor. The medical personnel review the CT images of the patient 14 and the target 46 to generate a plan for radiation treatment. The CT images can also assist in verifying the position of the target 46, such that the position of the patient 14 can be adjusted before treatment.

Figure 5:
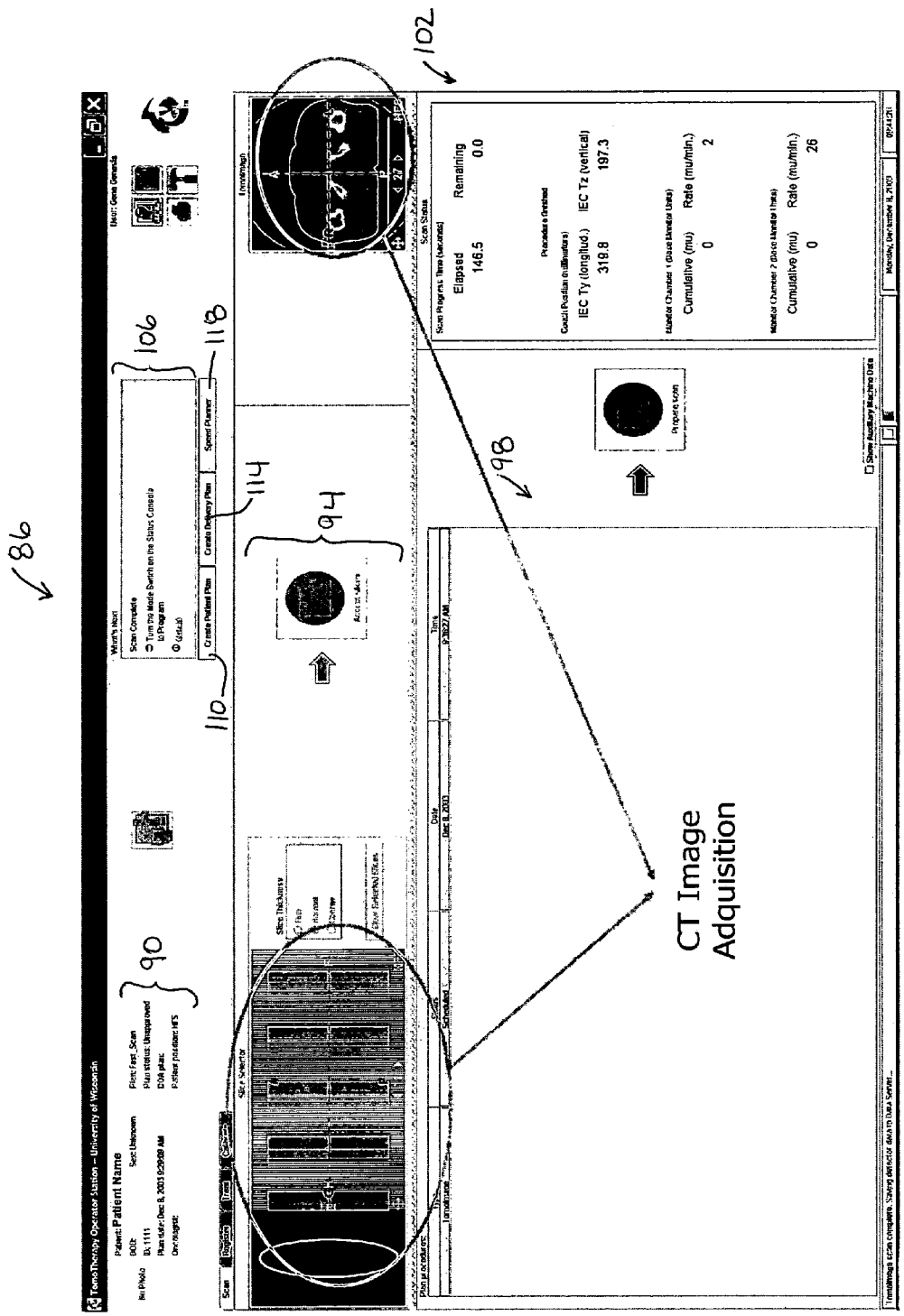
FIG. 5 is a screen shot generated by the software program of FIG. 4.

FIG. 5 illustrates an image acquisition screen 86, which medical personnel interact with to obtain the CT image data. The image acquisition screen 86 includes a patient identification section 90, which can include, for example, patient name, date of birth, sex, a picture of the patient, an identification number, a plan date, medical personnel (e.g., oncologist) name, the type of plan, the plan status, patient position, and the like. It is noted that additional information can be included on the image acquisition screen 86. It is also noted that less information can also be provided on the image acquisition screen 86.

The image acquisition screen 86 includes a slice selection section 94, which allows the medical personnel to select the width of each slice of the patient's body for each CT image. The image acquisition screen 86 also includes a CT image acquisition section 98, which displays the acquired CT image of the patient. The image acquisition screen 86 also includes a scan status section 102, which can include information, such as scan progress time, couch position, monitor chamber 1, and monitor chamber 2. The image acquisition screen 86 can also include a user instruction section 106, which informs the user what to do next in the radiation therapy treatment process, a create patient plan button 110, a create delivery plan button 114, and a speed planner button 118. The create patient plan button 110, the create delivery plan button 114, and the speed planner button 118 provide access to additional screens and functions of the software program 70. The screens associated with the create patient plan button 110 allow the medical personnel to contour and identify regions of interest, such as the target and avoidance region(s), usually compromising normal tissues and to assign treatment parameters describing the treatment. The screens associated with the create delivery plan button 114 allow the medical personnel to instruct the radiation therapy treatment system 10 to deliver the radiation treatment to the patient. The features and functionality of the speed planner button 118, when selected, are discussed below with respect to the contour module 86.

The software program 70 further includes a contour module 122 (FIG. 4) operable to generate geometric shapes, including three-dimensional shapes, that are used by medical personnel to identify treatment regions of the target 46 (regions of interest) and avoidance regions (regions at risk). The geometric shapes assist in defining the boundaries of the portion of the target 46 that will receive radiation and/or the portion of the target 46 that will receive minimal or no radiation. The medical personnel can use a plurality of the shapes to define the regions of interest and the regions at risk. The plurality of shapes can be used in a piecewise fashion to define irregular boundaries. Also, the medical personnel can identify the dose of radiation for the regions of interest and the regions at risk, and the number of fractions of the dose to be delivered to the patient 14.

It is noted that the contours can be generated by the user in a manual process (i.e., the user can draw contours by freehand), can be generated automatically or semi-automatically (i.e., the software program 70 can automatically recognize the regions of interest and/or the regions at risk to draw the contour), and/or can be generated in a deformation process. The user also can manually edit automatically generated contours. The contour module 122 can include a contour library of the contours used most often for a certain type of target 46, region of interest, and/or region at risk. The contour module 122 also can include one or more prototype contour sets that can be used for certain classes of patients and/or certain types of targets 46, regions of interest, and/or regions at risk.

In the deformation process, two images can be registered or morphed to take into account the differences or deformation of the images. For example, a first image can have a previously identified contour and the contour of the second image can be established by registering the second image with the first image taking into consideration deformation. In defining contours using a deformation process, various mathematical operations can be performed on the images, such as rotation, translation, scaling, shearing, and transformation.

The contours can be established and/or modified using a rolling ball, which is a graphical identification tool that controls the amount of detail in the contour. The rolling ball can be used to adjust the position and shape of the contour to achieve the desired radiation treatment. Contours can also be generated by combining or merging two or more contours to form a union of regions. The union of regions represents the areas of the contours that overlap. Contours can also be generated by combining two or more contours within their intersection point(s) to create a single contour. Union and intersection operations may be done multiple times in order to segment the contours.

Figure 6:
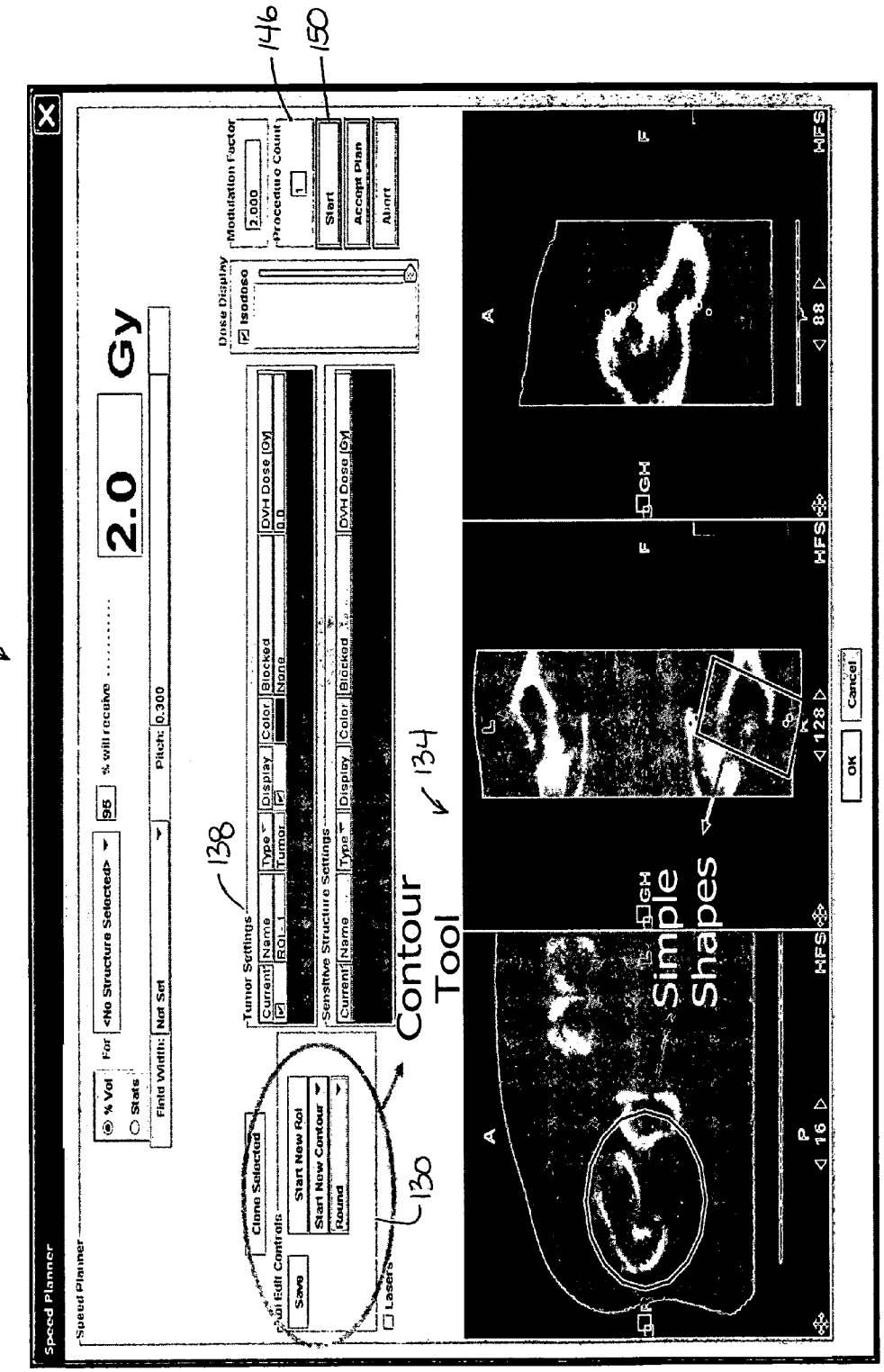
FIG. 6 is a screen shot generated by the software program of FIG. 4.

FIG. 6 illustrates a contour screen 126, which appears when medical personnel select the speed planner button 118 from the image acquisition screen 86. The medical personnel interact with the contour screen 126 to identify the regions of interest and/or the regions at risk. The contour screen 126 includes an edit section 130, which is used to select the geometric shape to identify a region of interest and/or a region at risk. The contour screen 126 includes an image section 134, which illustrates various views of the acquired CT images as described above. The image section 134 facilitates the identification of the regions of interest and the regions at risk with the selected geometric shapes. The size of the geometric shapes can be modified, for example, by dragging a computer mouse, to the appropriate size based on the size of the regions of interest and regions at risk. For example, FIG. 6 illustrates that a round geometric shape was selected to identify a region of interest (identified as ROI-1) in the transverse slice of the CT image (image on left). FIG. 6 also illustrates that a rectangular geometric shape was selected to identify a region of interest in the coronal view of the CT image (image in center).

The contour screen 126 also includes a tumor settings section 138 and a sensitive structure settings section 142. The tumor settings section 138 lists the various regions of interest identified by the medical personnel, a type, whether it is displayed, the color of the region of interest, whether any portion of the region is blocked from receiving radiation, and the dose for the region of interest. The sensitive structure settings section 142 lists regions at risk identified by the medical personnel, the type, whether it is displayed, the color of the region at risk, whether any portion of the region is blocked to receiving radiation, and the dose for the region at risk. The medical personnel can identify blocked or partially blocked directions to restrict the radiation beam 30. A blocked direction generally means that no primary beam will be allowed to go through that structure. A partially blocked direction generally means that the radiation will be allowed if the radiation beam 30 reaches the region of interest before reaching the region at risk. The tumor settings section 138 and the sensitive structure settings section 142 generally define the patient's prescription for radiation treatment. The contour screen 126 also includes a procedure count section 146, which represents the number of treatments the patient 14 will undergo. This number also represents the number of fractions into which the radiation dose will be divided. After the medical personnel has identified all of the desired regions of interest and the regions at risk, the medical personnel selects a start button 150 to initiate the automatic analysis of the entered data to generate a treatment plan.

The software program 70 also includes a treatment plan module 154 (FIG. 4) operable to generate a treatment plan for the patient 14 based on the data received from the contour module 122. The software program 70 analyzes the data from the contour module 122 and can automatically determine the radiation dose for each fraction or treatment based on the prescription entered on the contour screen 126 and the radiation dose for each of the regions of interest and the regions at risk based on the contours entered on the contour screen 126.

The treatment plan module 154 can apply a density correction to the CT images. In this process, the image density of the target 46 is translated to a physical density, which is useful for calculating dose. The physical density can also be obtained by assigning a density to the target 46 or it can be calculated by the computer 54 in an automated process from the CT image. The treatment plan can also be modified by a sub-optimization algorithm where an acceptable solution for radiation therapy is determined, but the time for preparation and delivery is reduced. This reduces the overall time it takes to treat the patient 14.

Figure 7:
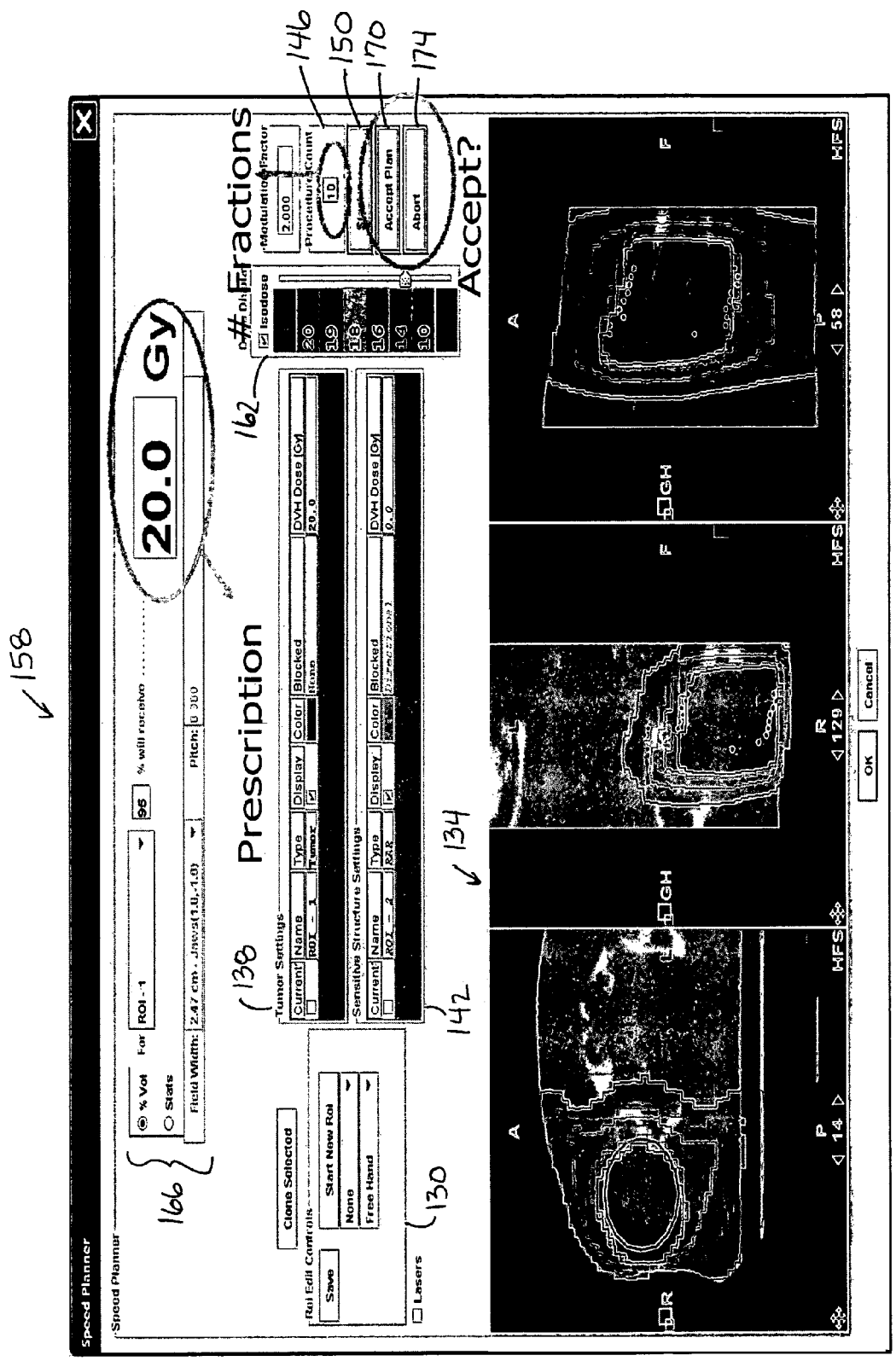
FIG. 7 is a screen shot generated by the software program of FIG. 4.

FIG. 7 illustrates a treatment plan screen 158, which medical personnel interact with to review, edit, and/or accept the generated treatment plan for the patient 14. The treatment plan screen 158 includes the edit section 130, the image section 134, the tumor settings section 138, the sensitive structure settings section 146, and the procedure count section, as well as other sections illustrated on the contour screen 126. The treatment plan screen 158 (and contour screen 126) includes a dose display section 162, which identifies the amount of radiation for each boundary around the region of interest for each treatment or fraction.

The image section 134 of the treatment plan screen 158 illustrates the various boundaries around the region of interest and the dose distribution to be delivered around the selected regions of interest. Each boundary around the region of interest is shaded (or color-coded) for ease of viewing. For example, FIG. 7 illustrates that the patient 14 will undergo 10 treatments and the innermost boundary of the region of interest (the tumor) will receive the most radiation, 21.4 Gy. Gy or gray is the measurement unit for absorbed dose of radiation. Each boundary around the innermost boundary of the region of interest will receive progressively less radiation. The outermost boundary will receive the least amount of radiation. The treatment plan screen 158 (and contour screen 126) includes a summary section 166, which indicates the amount of radiation the region of interest will receive based on percent volume. For example, FIG. 7 indicates that 95% of the tumor volume will receive 20.0 Gy. The summary section 166 also indicates a field width value and a pitch value for the linear accelerator 26. If the medical personnel accept the generated treatment plan, the medical personnel selects an accept plan button 170. The medical personnel can select an abort button 174 if the treatment plan is not acceptable.

Figure 8:
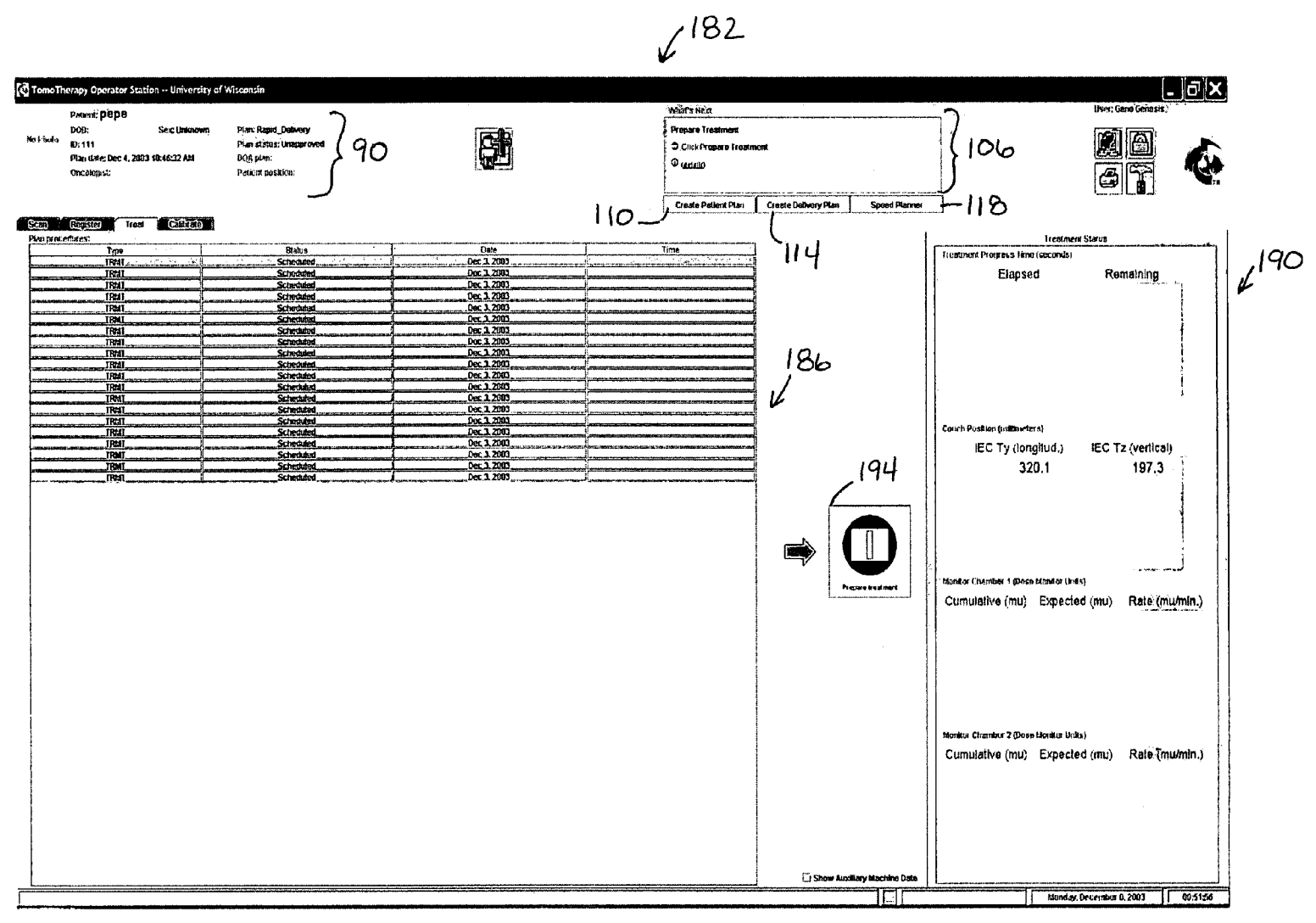

The software program 70 also includes a treatment delivery module 178 (FIG. 4) operable to instruct the radiation therapy treatment system to deliver the treatment plan for the patient 14 according to the treatment plan. The treatment delivery module 178 can utilize canonical, predetermined or template leaf patterns to generate the appropriate pattern for the radiation beam 30 based on the treatment parameters. The treatment delivery module 178 can also include a library of patterns for typical cases that can be accessed to compare with the present patient data in order to determine the pattern for the radiation beam 30. If the plan is accepted at the treatment plan screen 158, the treatment delivery module 178 generates a list of the number of fractions of the treatment plan to be delivered. FIG. 8 illustrates a treatment delivery screen 182, which identifies the number of treatments. The treatment delivery screen 182 includes the patient identification section 90, the user instruction section 106, the create patient plan button 110, the create delivery plan button 114, and the speed planner button 118 as well as other sections illustrated on the image acquisition screen 86. The treatment delivery screen 182 includes a plan procedure section 186, which identifies the number of treatments to be delivered to the patient. The plan procedure section 186 includes information such as the type of procedure, the status of the procedure, and the date and time of the procedure. The treatment delivery screen 182 also includes a treatment status section 190, which can include information, such as treatment progress time, couch position, monitor chamber 1, and monitor chamber 2.

Once the specific treatment is selected from the plan procedure section 186, the medical personnel can select a prepare treatment button 194. Based on the selected treatment and associated parameters, the treatment delivery module 178 can generate and transmit instructions to the gantry 18, the linear accelerator 26, the modulation device 34, and the couch drive system 66. The instructions coordinate the necessary movements of the gantry 18, the modulation device 34, and the couch drive system 66 to deliver the radiation beam 30 to the proper target in the proper amount as specified in the treatment plan.

The instructions for the modulation device 34 are determined or calculated by the treatment delivery module 178. The treatment delivery module 178 calculates the appropriate pattern, position, and intensity of the radiation beam 30 to be delivered, to match the prescription as provided on the contour screen 126. The pattern of the radiation beam 30 is generated by the modulation device 34, and more particularly by movement of the plurality of leaves in the multi-leaf collimator.

The software program 70 also includes a quality assurance module 198 (FIG. 4) operable to verify delivery of the dose to the patient 14. The quality assurance module 198 can generate quality assurance plans for phantoms. The quality assurance plans are generated to compare patient treatment plans to phantom treatment plans. The quality assurance plans can be implemented subsequent to delivery of one of the fractions of the treatment plan or before delivery of subsequent fractions of the treatment plan. The quality assurance module 198 can generate doses, radiation profiles, and other quality assurance metrics for arbitrary phantoms.

Multiple treatment plans with quality assurance variants can be generated to determine which one best fits the situation for a specific patient 14. The patient 14 can be scanned to acquire CT images with a phantom at a convenient location near the patient, such that the phantom is also scanned. A quality assurance plan can be generated for the phantom and can be the same as, or based on, a desired patient treatment plan. The delivery of the phantom treatment plan can verify dose delivery, while the patient 14 remains on the couch 62 awaiting delivery of the treatment plan.

A multiple pass with quality assurance variants can be generated to divide the delivery of a fraction of the treatment plan into several sub-fractions. A first sub-fraction of the fraction can be delivered to the patient 14 and a measurement device can be positioned on or near the patient 14 to record radiation delivery. The measured radiation can be compared to predetermined radiation delivery values, and if they are similar, the remaining sub-fractions of the fraction can be delivered to the patient 14.

Figure 9:
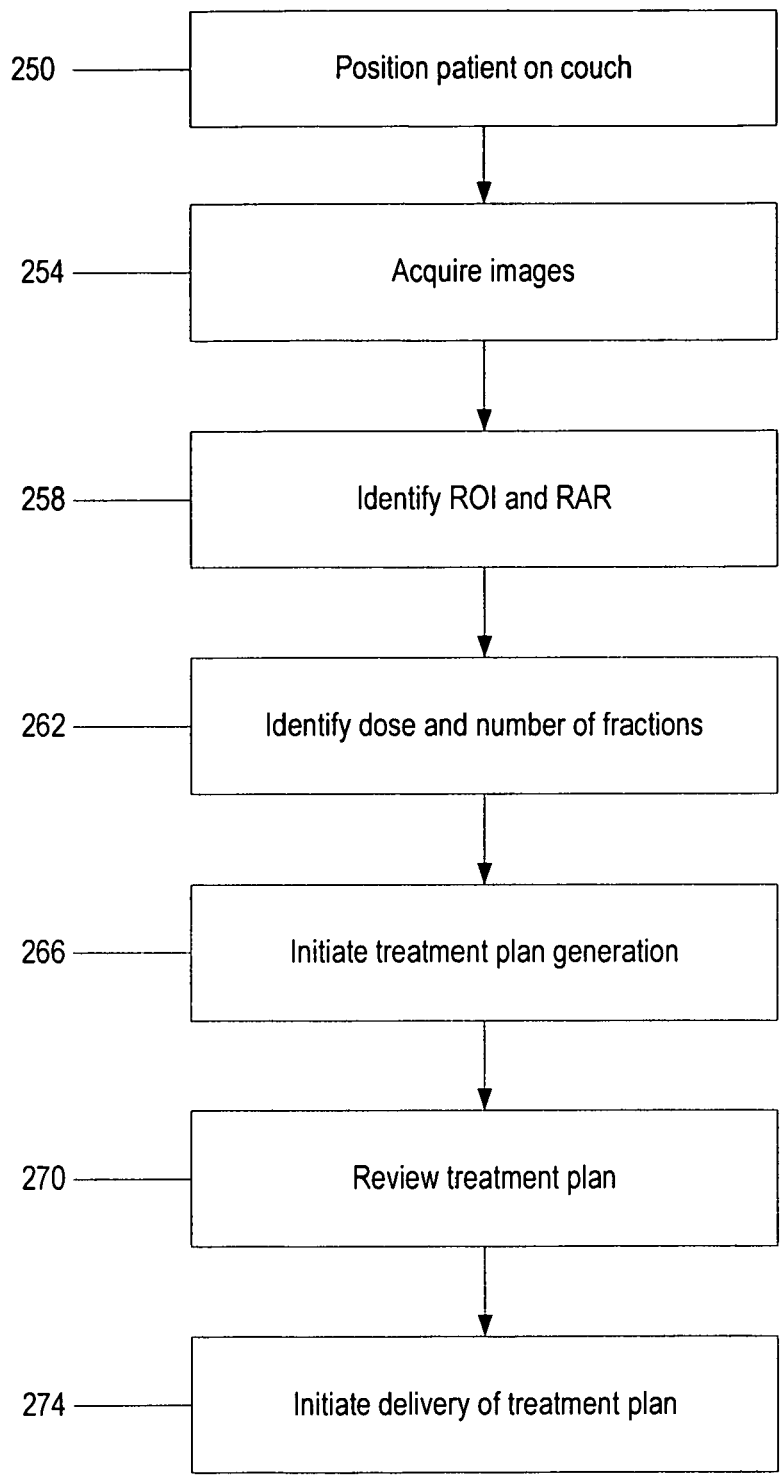
FIG. 9 is a flow chart illustrating a radiation therapy treatment process using the radiation therapy treatment system of FIG. 1 according to one embodiment of the method of the invention.

FIG. 9 illustrates a flow chart of a method of treating a patient with radiation therapy according to one embodiment of the invention. The patient 14 is positioned (at 250) on the couch 62. The medical personnel utilize the image acquisition module 82 of the software program 70 to acquire (at 254) CT images of the target 46. It is noted that the CT images can be acquired by radiation therapy linear accelerator or by other equipment that is essentially integrated or attached to the radiation treatment therapy system 10. The medical personnel review the CT images and utilize the geometric shapes of the contour module 122 of the software program 70 to identify (at 258) the regions of interest and/or regions at risk. The medical personnel identify (at 262) the dose for the regions of interest and/or regions at risk and the number of fractions. The medical personnel then initiate (at 266) the generation of a treatment plan by the treatment plan module 154 of the software program 70. After review (at 270) and approval of the treatment plan, the medical personnel initiate (at 274) delivery of the treatment plan. The treatment plan can be delivered to the patient 14 numerous times based on the number of fractions. For delivery of future fractions of the treatment plan, the originally acquired CT images can be used as the reference image for positioning of the patient 14. The patient 14 can also be positioned for the delivery of future fractions of the treatment plan based on the dose distribution based on the first delivered fraction, the contours of the first delivered fraction, or any images, dose distributions, or contours from subsequently delivered fractions.

Figure 10:
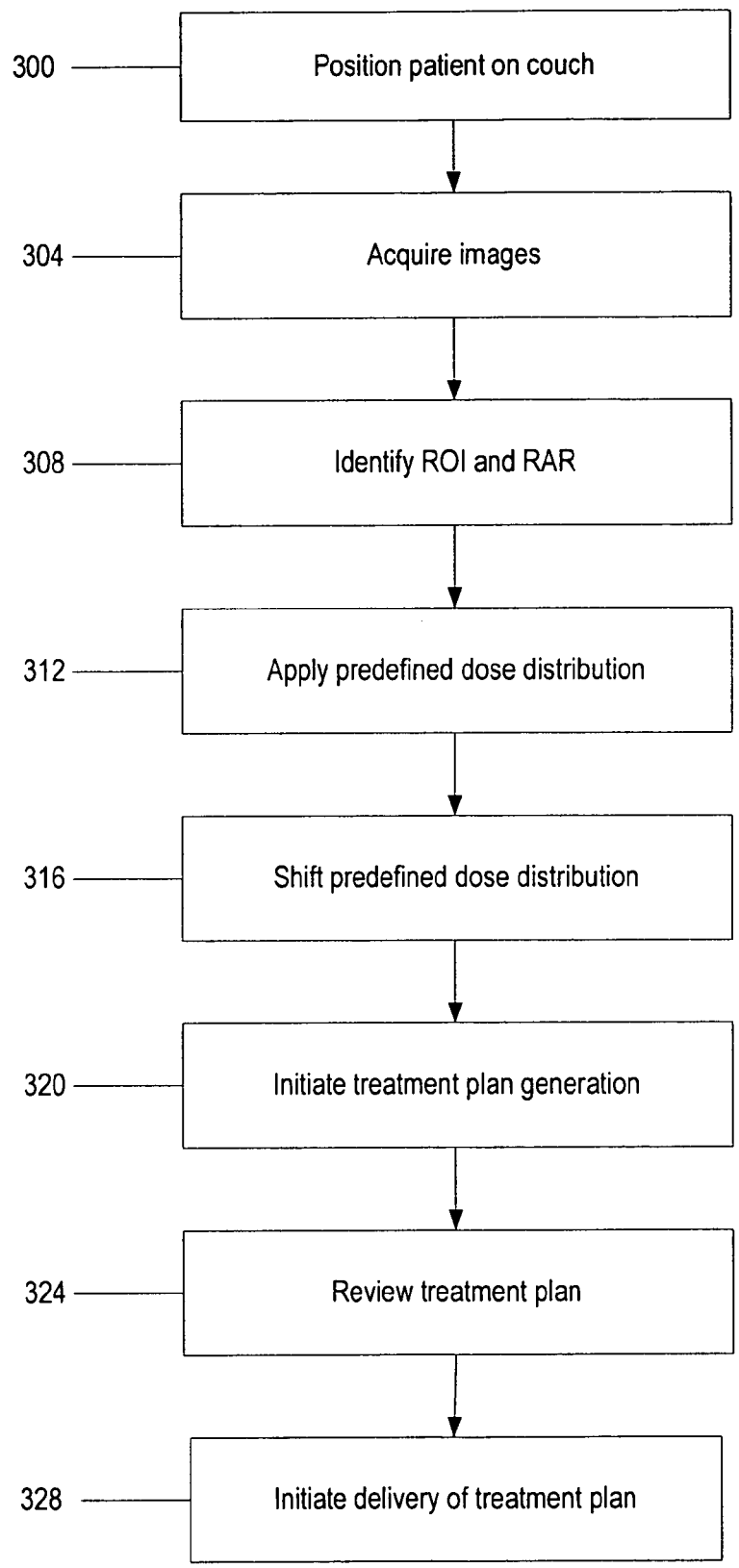
FIG. 10 is a flow chart illustrating a radiation therapy treatment process using the radiation therapy treatment system of FIG. 1 according to one embodiment of the method of the invention.

FIG. 10 illustrates a flow chart of a method of treating a patient with radiation therapy according to one embodiment of the invention. The patient 14 is positioned (at 300) on the couch 62. The medical personnel utilize the image acquisition module 82 of the software program 70 to acquire (at 304) CT images of the target 46. It is noted that the CT images can be acquired by radiation therapy linear accelerator or by other equipment that is essentially integrated or attached to the radiation treatment therapy system 10. The medical personnel review the CT images and utilize the geometric shapes of the contour module 122 of the software program 70 to identify (at 308) the regions of interest and/or regions at risk. The medical personnel apply (at 312) a predefined dose distribution to the defined regions of interest and/or regions at risk. The contour module 122 shifts (at 316) the predefined dose distribution based on the selected shapes used to define the regions of interest and/or regions at risk. The medical personnel then initiate (at 320) the generation of a treatment plan by the treatment plan module 154 of the software program 70. After review (at 324) and approval of the treatment plan, the medical personnel initiate (at 328) delivery of the treatment plan. The treatment plan can be delivered to the patient 14 numerous times based on the number of fractions. For delivery of future fractions of the treatment plan, the originally acquired CT images can be used as the reference image for positioning of the patient 14. The patient 14 can also be positioned for the delivery of future fractions of the treatment plan based on the dose distribution based on the first delivered fraction, the contours of the first delivered fraction, or any images, dose distributions, or contours from subsequently delivered fractions.

After the patient's first treatment, the same treatment plan can be used for future treatments. Subsequent fractions of the treatment plan can be modified or optimized. For example, the treatment plan can be modified to account for anatomical changes and to remedy errors in the process. In addition, subsequent fractions of the treatment plan can be modified to account for cumulative dose delivered to regions of interest and/or regions at risk. The fractions of the treatment plan can be modified to incorporate the effects of deformation and biological information. The fractions of the treatment plan can be additionally modified based on the initial acquired CT images or based on subsequently acquired CT images.

The radiation therapy treatment system 10 integrates positioning of the patient, treatment planning, and delivery of the plan in a single system or essentially the same system or apparatus. There is no need to transport the patient 14 to numerous departments in a medical facility for radiation therapy. As a result of the system integration and use of geometric shapes to identify contours, a patient 14 can be treated in approximately 20 minutes or less. For example, it should take about two minutes to position the patient 14 on the couch 62, about three to about six minutes to acquire the CT images, about three minutes to identify the contours, about two minutes to generate the treatment plan, and about three minutes to deliver the plan.

Figure 11:
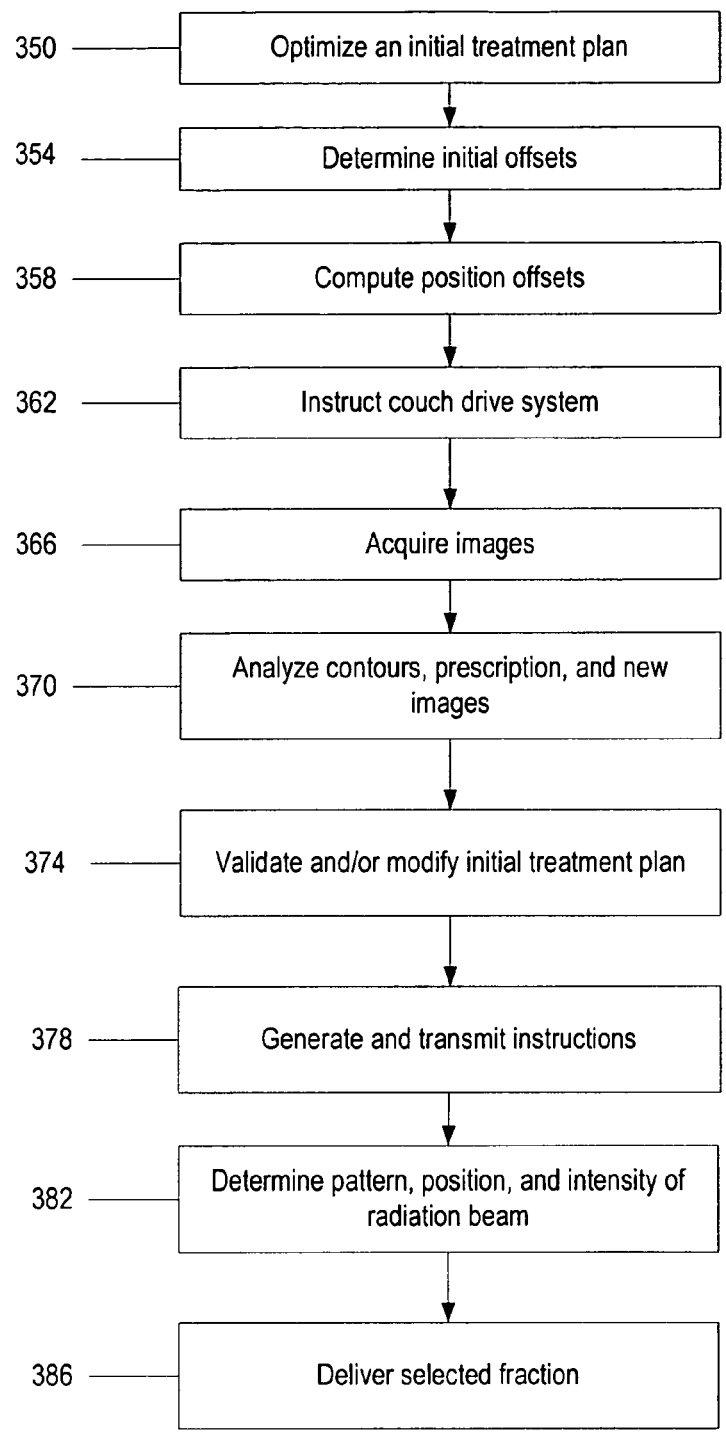
FIG. 11 is a flow chart illustrating operation of the software program of FIG. 4 according to one embodiment of the method of the invention.

FIG. 11 illustrates a flow chart of a method of operation of the software program 70 according to one embodiment of the invention. After collecting image data and generating an initial plan for the patient, the initial plan is (at 350) optimized on a separate apparatus. The patient 14 is positioned on the couch 62 for a treatment. The patient positioning module 78 determines (at 354) initial offsets between fiducial markers on the patient and the isocenter of the gantry 18. The patient positioning module 78 utilizes a laser system in the patient room to help determine these offsets. The patient positioning module 78 computes (at 358) the position offsets from the final treatment position using the initial offsets. The patient positioning module 78 instructs (at 362) the couch drive system 66 to move to the ready position, so that the target 46 isocenter is aligned vertically with the gantry isocenter, and the first slice to be obtained is just before the isocentric plane (this allows room for the gantry 18 to start rotating before the first slice).

After patient alignment, the image acquisition module 82 acquires (at 366) images of the patient 14 using a helical scan procedure (e.g., the couch 62 moves into the opening of the gantry 18 as the gantry rotates about the patient 14). The medical personnel reviews the images to identify the regions of interest and/or the regions at risk. The treatment plan module 154 analyzes (at 370) the contours, the prescription, and/or the new images and validates (at 374) and/or modifies the initial treatment plan as appropriate. If the treatment plan is acceptable, the treatment delivery module 178 generates and transmits (at 378) instructions to the gantry 18, the linear accelerator 26, the modulation device 34, and the couch drive system 66. The treatment delivery module 178 also determines (at 382) the appropriate pattern, position, and intensity of the radiation beam 30 to be delivered, to match the treatment plan. The treatment delivery module 178 delivers (at 386) the selected fraction of the treatment plan to the patient 14 using a helical delivery procedure.

Various features and advantages of the invention are set forth in the following claims.

What is claimed is:

1. A method of treating a patient with radiation, the method comprising:
    acquiring three-dimensional image data from the patient using a radiation source while the patient is in a treatment position;
    defining a target region while the patient remains in the treatment position;
    generating an initial contour set for the target region from one of a contour library and a prototype contour set;
    generating a treatment plan based on the defined target region and the three-dimensional image data while the patient remains in the treatment position; and
    while the patient remains in the treatment position, delivering radiation to the target region using the radiation source according to the treatment plan.

2. The method of claim 1, wherein the target region is defined using one or more predefined shapes.

3. The method of claim 1 further comprising the act of defining an avoidance region with one or more predefined shapes.

4. The method of claim 1 further comprising the act of defining an amount of radiation to be delivered to the target region.

5. The method of claim 4 further comprising the act of generating a dose distribution based on the amount of radiation to be delivered to the target region.

6. The method of claim 5 further comprising the act of generating a number of treatment fractions based on the dose distribution.

7. The method of claim 1 wherein the target region is an irregular shape and wherein a plurality of the predefined shapes can be used to define the irregular shape.

8. The method of claim 1 wherein the act of defining a target region includes the act of utilizing at least one predefined shape to define the target region in a transverse slice of the image data.

9. The method of claim 8 wherein the act of defining a target region includes the act of automatically defining the target region three-dimensional space based on two-dimensional contours drawn in any combinations of coronal slice planes, sagittal slice planes, and transverse slice planes.

10. The method of claim 1 wherein the target contour is manually edited.

11. The method of claim 1 wherein the generation of contours uses deformable registration.

12. The method of claim 1 wherein the image data is acquired using a radiation therapy system having an imaging apparatus.

13. The method of claim 12 wherein the image data is acquired with a radiation beam having a fan-shaped geometry.

14. The method of claim 12 wherein the image data is acquired with a radiation beam having a multi-slice geometry.

15. The method of claim 12 wherein the image data is acquired with a radiation beam having a cone-beam geometry.

16. The method of claim 12 wherein the imaging apparatus uses megavoltage energies.

17. The method of claim 12 wherein the imaging apparatus uses kilovoltage energies.

18. The method of claim 12 wherein the imaging apparatus uses emitted photons.

19. The method of claim 12 wherein the imaging apparatus is a magnetic resonance imaging system.

20. The method of claim 1 wherein the act of acquiring image data includes the act of pre-processing the image data to generate the treatment plan.

21. The method of claim 20 wherein the act of pre-processing the image data includes adjusting the density content of the image data.

22. The method of claim 1 wherein the act of delivering radiation to the target region includes the act of delivering photon radiation.

23. The method of claim 1 wherein the act of delivering radiation to the target region includes the act of delivering proton radiation.

24. The method of claim 1 wherein the act of delivering radiation to the target region includes the act of delivering therapeutic particle radiation.

25. The method of claim 1 wherein the act of generating the treatment plan includes the act of incorporating previously delivered dose information.

26. The method of claim 1 wherein the patient remains substantially stationary between the act of acquiring image data from the patient and the act of delivering radiation to the target region.

27. The method of claim 1 wherein the patient lies on a platform, and wherein the patient remains on the platform between the act of acquiring image data from the patient and the act of delivering radiation to the target region.

28. The method of claim 1 wherein the act of generating the treatment plan includes generating a conformal treatment plan and further comprises the act of optimizing the conformal treatment plan.

29. The method of claim 1 wherein the act of generating the treatment plan includes generating an IMRT treatment plan and further comprises the act of optimizing the IMRT treatment plan.

30. The method of claim 1 wherein the treatment plan is used for subsequent treatment fractions.

31. The method of claim 1 wherein the act of generating the treatment plan includes the act of utilizing class solutions.

32. The method of claim 1 wherein the act of generating the treatment plan includes the act of utilizing optimization templates.

33. The method of claim 1 wherein the act of generating the treatment plan includes the act of performing a pre-determined number of iterations.

34. The method of claim 1 further comprising the act of acquiring subsequent image data and the act of generating a subsequent treatment plan based on the subsequently acquired image data.

35. The method of claim 34 wherein the subsequent treatment plan is based at least partially on one or more previous treatment plans.

36. The method of claim 35 wherein the act of generating the treatment plan includes the act of utilizing a biological model.

37. The method of claim 34 wherein the subsequent treatment plan is based at least partially on a previously delivered dose to the patient.

38. The method of claim 37 wherein the previously delivered dose includes an accumulation of a plurality of doses, and wherein the plurality of doses is determined based on a deformation process.

39. The method of claim 1 further comprising the act of generating a subsequent treatment plan, and wherein the subsequent treatment plan includes at least one treatment fraction, wherein the subsequent treatment plan is optimized for at least one treatment fraction.

40. The method of claim 1 wherein the treatment plan includes at least two treatment fractions, and wherein the patient is aligned for delivery of the second treatment fraction using the image data.

41. The method of claim 1 wherein the treatment plan includes at least two treatment fractions, and wherein the patient is positioned for delivery of the second treatment fraction using one of contour information, image information, and dosimetric information.

42. The method of claim 1 further comprising the act of generating a quality assurance plan adapted to validate a dose delivery in a phantom.

43. The method of claim 42 wherein the treatment plan includes a plurality of fractions, and further comprising the act of dividing one of the fractions into a first sub-fraction and a second sub-fraction, and wherein the treatment plan dosimetry is validated after delivery of the first sub-fraction and before completing delivery of the second sub-fraction.

44. The method of claim 1 wherein the radiation source is in communication with an integrated database.

45. The method of claim 1 wherein the radiation source includes a single source point for a radiation beam used in the acquisition of image data from the patient and a radiation beam used in the delivery of radiation to the target region.

46. The method of claim 1 wherein the acquiring, defining, generating an initial contour set, generating a treatment plan, and delivering acts can be completed in less than thirty minutes.

47. The method of claim 1 wherein the radiation source includes a first source point for a radiation beam used in the acquisition of image data from the patient and a second source point for a radiation beam used in the delivery of radiation to the target region.

48. A method of treating a patient with radiation, the method comprising:
    acquiring three-dimensional image data from the patient using a radiation source while the patient is in a treatment position;
    defining a target region while the patient remains in the treatment position;
    generating a treatment plan based on the defined target region and the three-dimensional image data while the patient remains in the treatment position;
    while the patient remains in the treatment position, delivering radiation to the target region using the radiation source according to the treatment plan;
    acquiring subsequent image data; and
    generating a subsequent treatment plan based on the subsequently acquired image data, wherein the subsequent treatment plan is based at least partially on a previously delivered dose to the patient, and
    wherein the previously delivered dose includes an accumulation of a plurality of doses, and wherein the plurality of doses is determined based on a deformation process.

49. The method of claim 48, wherein the target region is defined using one or more predefined shapes.

50. The method of claim 48 wherein the patient remains substantially stationary between the act of acquiring image data from the patient and the act of delivering radiation to the target region.

51. The method of claim 48 wherein the patient lies on a platform, and wherein the patient remains on the platform between the act of acquiring image data from the patient and the act of delivering radiation to the target region.

52. The method of claim 48 wherein the radiation source includes a single source point for a radiation beam used in the acquisition of image data from the patient and a radiation beam used in the delivery of radiation to the target region.

53. The method of claim 48 wherein the radiation source includes a first source point for a radiation beam used in the acquisition of image data from the patient and a second source point for a radiation beam used in the delivery of radiation to the target region.

54. A method of treating a patient with radiation, the method comprising:
    acquiring three-dimensional image data from the patient using a radiation source while the patient is in a treatment position;
    defining a target region while the patient remains in the treatment position;
    generating a treatment plan based on the defined target region and the three-dimensional image data while the patient remains in the treatment position; and
    while the patient remains in the treatment position, delivering radiation to the target region using the radiation source according to the treatment plan, and
    wherein the act of acquiring image data includes the act of pre-processing the image data to generate the treatment plan, and
    wherein the act of pre-processing the image data includes adjusting the density content of the image data.

55. The method of claim 54, wherein the target region is defined using one or more predefined shapes.

56. The method of claim 54 further comprising the act of defining an avoidance region with one or more predefined shapes.

57. The method of claim 54 further comprising the act of defining an amount of radiation to be delivered to the target region.

58. The method of claim 57 further comprising the act of generating a dose distribution based on the amount of radiation to be delivered to the target region.

59. The method of claim 58 further comprising the act of generating a number of treatment fractions based on the dose distribution.

60. The method of claim 54 wherein the target region is an irregular shape and wherein a plurality of the predefined shapes can be used to define the irregular shape.

61. The method of claim 54 wherein the act of defining a target region includes the act of utilizing at least one predefined shape to define the target region in a transverse slice of the image data.

62. The method of claim 61 wherein the act of defining a target region includes the act of automatically defining the target region three-dimensional space based on two-dimensional contours drawn in any combinations of coronal slice planes, sagittal slice planes, and transverse slice planes.

63. The method of claim 54 wherein the act of defining a target region includes the act of using an automatically generated contour.

64. The method of claim 63 wherein the automatically generated contour is adapted to be manually edited.

65. The method of claim 54 wherein an initial contour set is generated from one of a contour library and a prototype contour set.

66. The method of claim 65 wherein the generation of contours uses deformable registration.

67. The method of claim 66 wherein the image data is acquired using a radiation therapy system having an imaging apparatus.

68. The method of claim 67 wherein the image data is acquired with a radiation beam having a fan-shaped geometry.

69. The method of claim 67 wherein the image data is acquired with a radiation beam having a multi-slice geometry.

70. The method of claim 67 wherein the image data is acquired with a radiation beam having a cone-beam geometry.

71. The method of claim 67 wherein the imaging apparatus uses megavoltage energies.

72. The method of claim 67 wherein the imaging apparatus uses kilovoltage energies.

73. The method of claim 67 wherein the imaging apparatus uses emitted photons.

74. The method of claim 67 wherein the imaging apparatus is a magnetic resonance imaging system.

75. The method of claim 54 wherein the act of delivering radiation to the target region includes the act of delivering photon radiation.

76. The method of claim 54 wherein the act of delivering radiation to the target region includes the act of delivering proton radiation.

77. The method of claim 54 wherein the act of delivering radiation to the target region includes the act of delivering therapeutic particle radiation.

78. The method of claim 54 wherein the act of generating the treatment plan includes the act of incorporating previously delivered dose information.

79. The method of claim 54 wherein the patient remains substantially stationary between the act of acquiring image data from the patient and the act of delivering radiation to the target region.

80. The method of claim 54 wherein the patient lies on a platform, and wherein the patient remains on the platform between the act of acquiring image data from the patient and the act of delivering radiation to the target region.

81. The method of claim 54 wherein the act of generating the treatment plan includes generating a conformal treatment plan and further comprises the act of optimizing the conformal treatment plan.

82. The method of claim 54 wherein the act of generating the treatment plan includes generating an IMRT treatment plan and further comprises the act of optimizing the IMRT treatment plan.

83. The method of claim 54 wherein the treatment plan is used for subsequent treatment fractions.

84. The method of claim 54 wherein the act of generating the treatment plan includes the act of utilizing class solutions.

85. The method of claim 54 wherein the act of generating the treatment plan includes the act of utilizing optimization templates.

86. The method of claim 54 wherein the act of generating the treatment plan includes the act of performing a pre-determined number of iterations.

87. The method of claim 54 further comprising the act of acquiring subsequent image data and the act of generating a subsequent treatment plan based on the subsequently acquired image data.

88. The method of claim 87 wherein the subsequent treatment plan is based at least partially on one or more previous treatment plans.

89. The method of claim 88 wherein the act of generating the treatment plan includes the act of utilizing a biological model.

90. The method of claim 87 wherein the subsequent treatment plan is based at least partially on a previously delivered dose to the patient.

91. The method of claim 90 wherein the previously delivered dose includes an accumulation of a plurality of doses, and wherein the plurality of doses is determined based on a deformation process.

92. The method of claim 54 further comprising the act of generating a subsequent treatment plan, and wherein the subsequent treatment plan includes at least one treatment fraction, wherein the subsequent treatment plan is optimized for at least one treatment fraction.

93. The method of claim 54 wherein the treatment plan includes at least two treatment fractions, and wherein the patient is aligned for delivery of the second treatment fraction using the image data.

94. The method of claim 54 wherein the treatment plan includes at least two treatment fractions, and wherein the patient is positioned for delivery of the second treatment fraction using one of contour information, image information, and dosimetric information.

95. The method of claim 54 further comprising the act of generating a quality assurance plan adapted to validate a dose delivery in a phantom.

96. The method of claim 95 wherein the treatment plan includes a plurality of fractions, and further comprising the act of dividing one of the fractions into a first sub-fraction and a second sub-fraction, and wherein the treatment plan dosimetry is validated after delivery of the first sub-fraction and before completing delivery of the second sub-fraction.

97. The method of claim 54 wherein the radiation source is in communication with an integrated database.

98. The method of claim 54 wherein the radiation source includes a single source point for a radiation beam used in the acquisition of image data from the patient and a radiation beam used in the delivery of radiation to the target region.

99. The method of claim 54 wherein the acquiring, defining, generating an initial contour set, generating a treatment plan, and delivering acts can be completed in less than thirty minutes.

100. The method of claim 54 wherein the radiation source includes a first source point for a radiation beam used in the acquisition of image data from the patient and a second source point for a radiation beam used in the delivery of radiation to the target region.

* * * * *